United States Patent
Astier et al.

(10) Patent No.: US 9,975,147 B2
(45) Date of Patent: May 22, 2018

(54) CONTINUOUS FLOW, SIZE-BASED SEPARATION OF ENTITIES DOWN TO THE NANOMETER SCALE USING NANOPILLAR ARRAYS

(71) Applicant: International Business Machines Corporation, Armonk, NY (US)

(72) Inventors: Yann A. Astier, White Plains, NY (US); Joshua T. Smith, Croton-on-Hudson, NY (US); Gustavo A. Stolovitzky, Riverdale, NY (US); Chao Wang, Yorktown Heights, NY (US); Benjamin H. Wunsch, Yorktown Heights, NY (US)

(73) Assignee: INTERNATIONAL BUSINESS MACHINES CORPORATION, Armonk, NY (US)

( * ) Notice: Subject to any disclaimer, the term of this patent is extended or adjusted under 35 U.S.C. 154(b) by 16 days.

(21) Appl. No.: 14/749,309

(22) Filed: Jun. 24, 2015

(65) Prior Publication Data
US 2016/0144406 A1 May 26, 2016

Related U.S. Application Data

(63) Continuation of application No. 14/697,072, filed on Apr. 27, 2015.
(Continued)

(51) Int. Cl.
*B07B 1/00* (2006.01)
*B07B 13/04* (2006.01)
(Continued)

(52) U.S. Cl.
CPC ............ *B07B 13/04* (2013.01); *B07B 1/4609* (2013.01); *B82Y 30/00* (2013.01); *G01N 15/02* (2013.01);
(Continued)

(58) Field of Classification Search
CPC ............ B07B 4/02; B01D 21/245; B03B 5/00; G01N 27/447; G01N 27/44756;
(Continued)

(56) References Cited

U.S. PATENT DOCUMENTS

| 6,881,315 B2* | 4/2005 | Iida .................. B01L 3/502761 204/164 |
| 8,783,466 B2* | 7/2014 | Han ...................... B01D 61/027 204/450 |
| 2010/0006479 A1* | 1/2010 | Reichenbach ......... B01D 43/00 209/132 |
| 2015/0361489 A1* | 12/2015 | Soper .................. G01N 27/4473 506/4 |

OTHER PUBLICATIONS

List of IBM Patents or Patent Applications Treated As Related—Date Filed: Feb. 19, 2016; 1 page.
(Continued)

*Primary Examiner* — Joseph C Rodriguez
*Assistant Examiner* — Kalyanavenkateshware Kumar
(74) *Attorney, Agent, or Firm* — Cantor Colburn LLP; Vazken Alexanian

(57) ABSTRACT

A technique relates sorting entities. The entities are introduced into a nanopillar array. The entities include a first population and a second population, and the nanopillar array includes nanopillars arranged to have a gap separating one from another. The nanopillars are ordered to have an array angle relative to a fluid flow direction. The entities are sorted through the nanopillar array by transporting the first population of the entities less than a predetermined size in a first direction and by transporting the second population of the entities at least the predetermined size in a second direction different from the first direction. The nanopillar array is configured to employ the gap with a gap size less than 300 nanometers in order to sort the entities having a sub-100 nanometer size.

9 Claims, 22 Drawing Sheets

Related U.S. Application Data

(60) Provisional application No. 62/084,647, filed on Nov. 26, 2014.

(51) Int. Cl.
*B07B 1/46* (2006.01)
*G01N 15/00* (2006.01)
*B82Y 30/00* (2011.01)
*G01N 15/02* (2006.01)

(52) U.S. Cl.
CPC ............... *G01N 2015/0065* (2013.01); *G01N 2015/0288* (2013.01); *Y10S 977/84* (2013.01)

(58) Field of Classification Search
CPC ......... G01N 27/44791; G01N 30/0005; G01N 30/6069; G01N 30/6095; G01N 2030/528; B01L 3/502753
USPC ........ 209/134, 136, 138, 142, 143, 209, 210
See application file for complete search history.

(56) References Cited

OTHER PUBLICATIONS

Y. Astier, et al., "Biopolymer Separation Using Nanostructured Arrays," U.S. Appl. No. 14/697,269, filed Apr. 27, 2015.

Y. Astier, et al., "Continuous Flow, Size-Based Separation of Entities Down to the Nanometer Scale Using Nanopillar Arrays," U.S. Appl. No. 14/697,072, filed Apr. 27, 2015.

Y. Astier, et al., "Pillar Array Structure with Uniform and High Aspect Ratio Nanometer Gaps," U.S. Appl. No. 14/697,095, filed Apr. 27, 2015.

Yann A. Astier, et al.; "Bipolymer Separation Using Nanostructured Arrays"; U.S. Appl. No. 14/749,202, filed Jun. 24, 2015.

Yann A. Astier, et al.; "Pillar Array Structure With Unifor and High Aspect Ratio Nanometer Gaps"; U.S. Appl. No. 14/749,123, filed Jun. 24, 2015.

\* cited by examiner

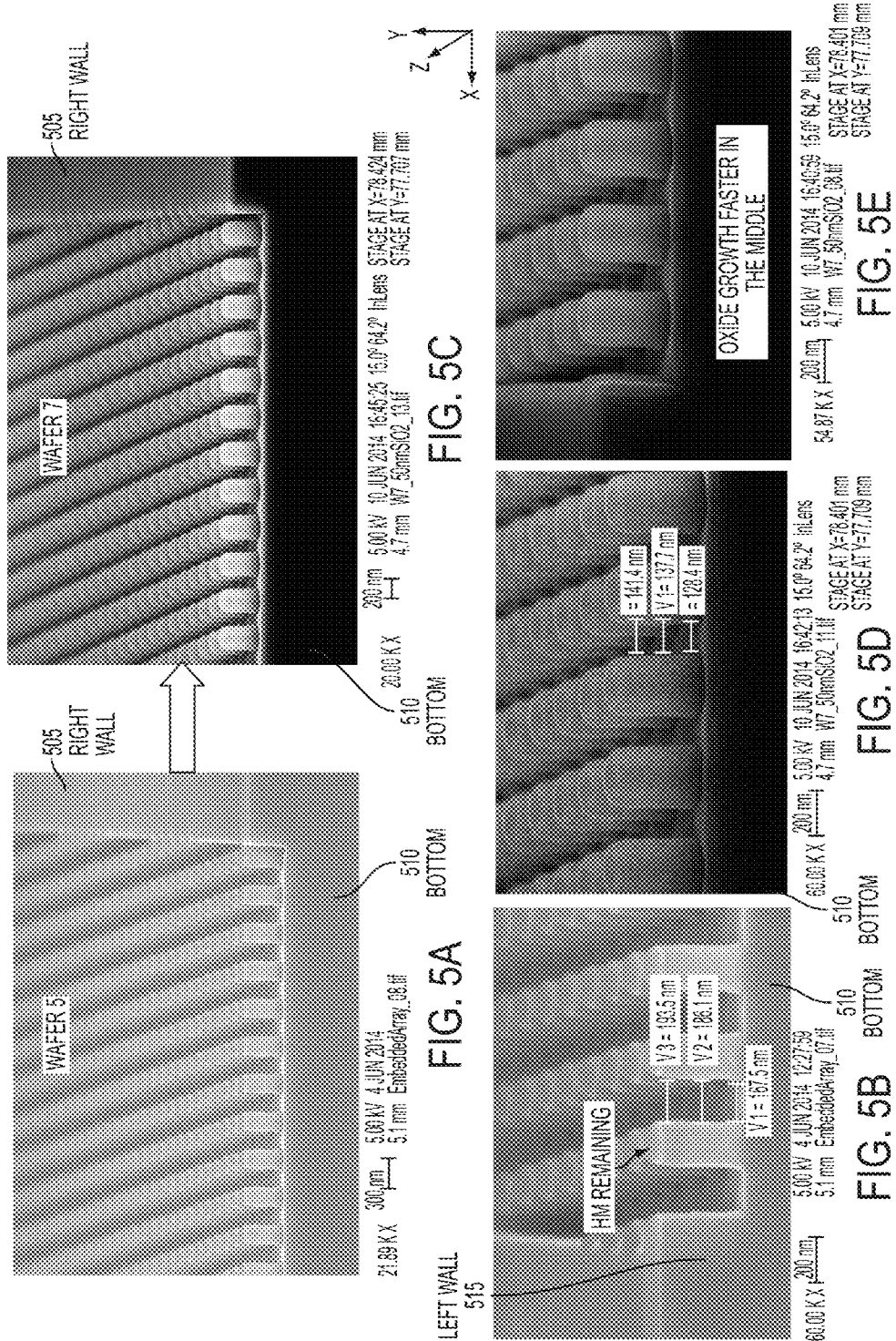

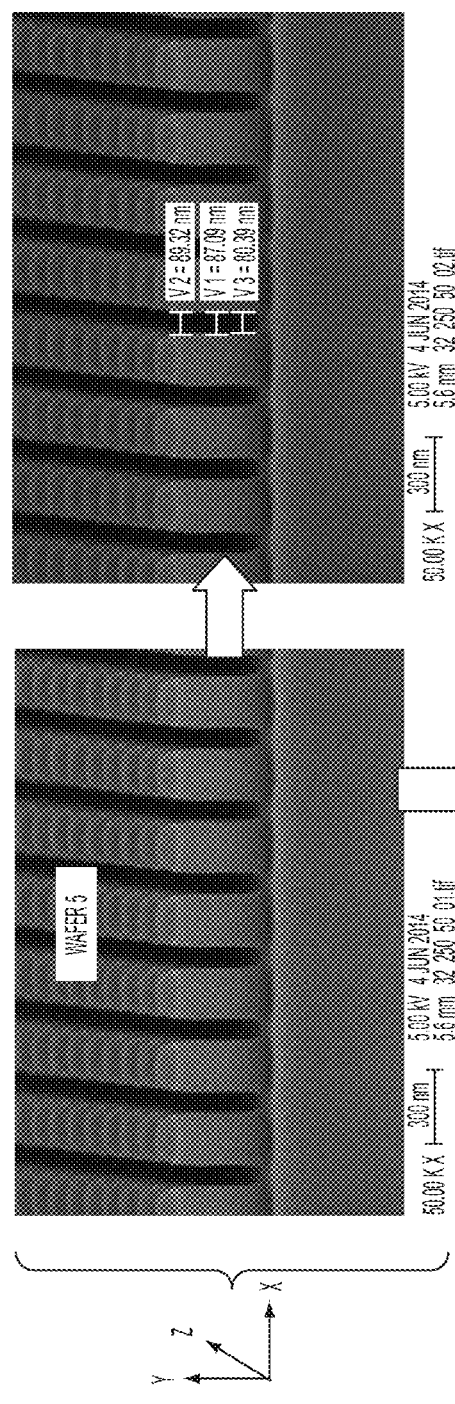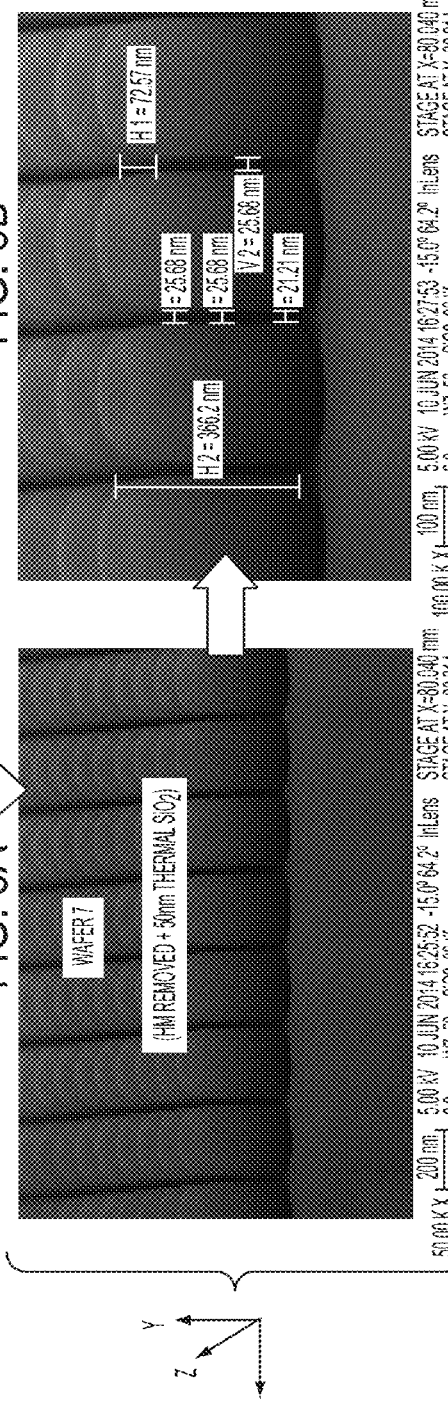
FIG. 6A
FIG. 6B
FIG. 6C
FIG. 6D

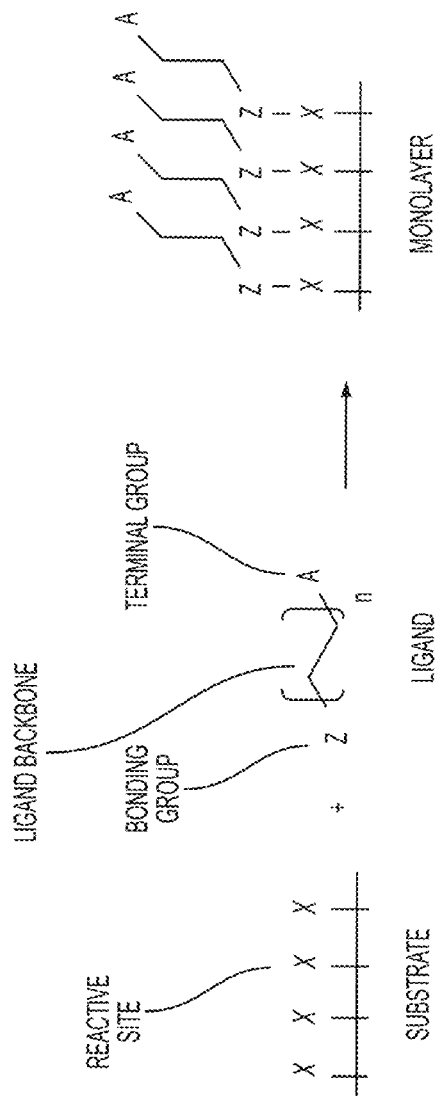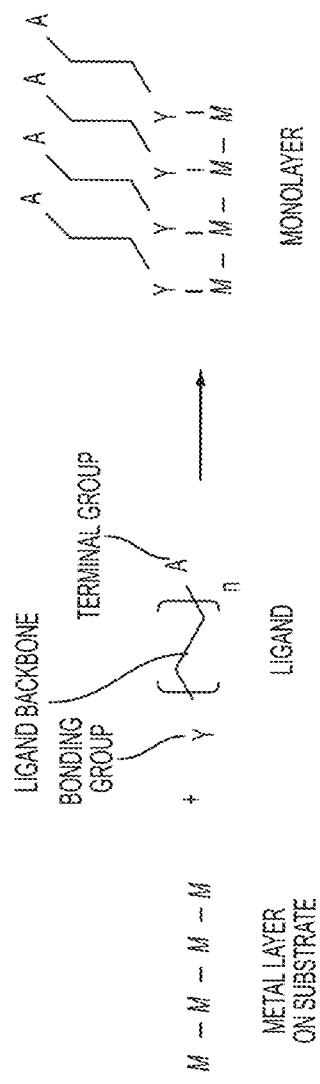
FIG. 7A
FIG. 7B

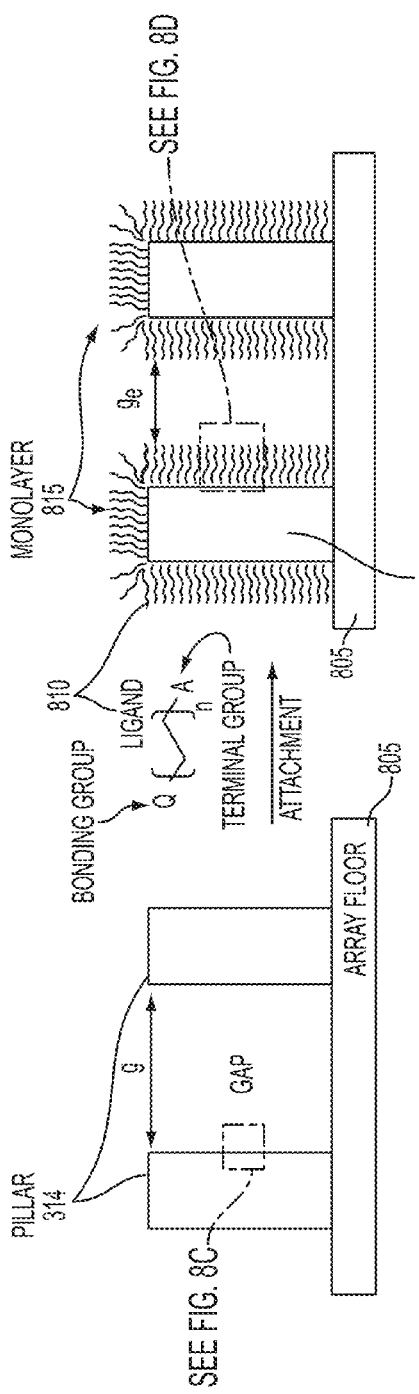
FIG. 8A
FIG. 8B
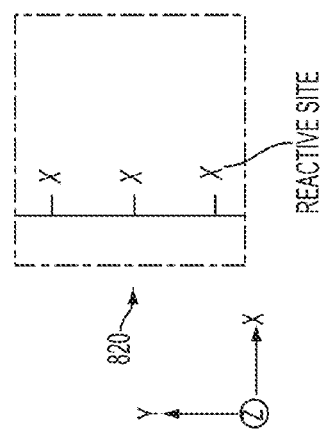
FIG. 8C
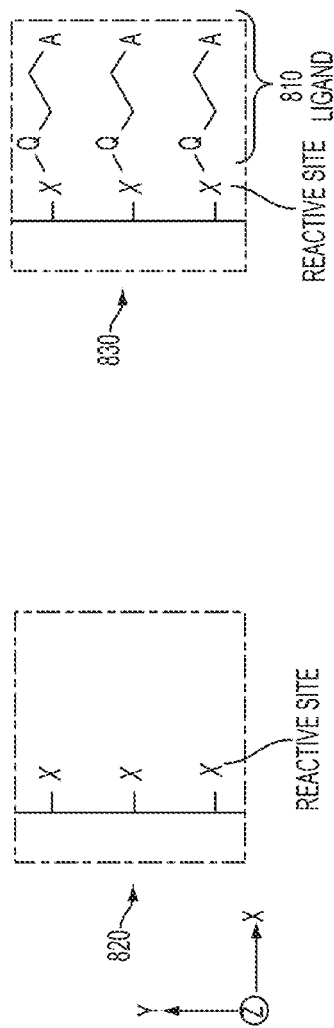
FIG. 8D

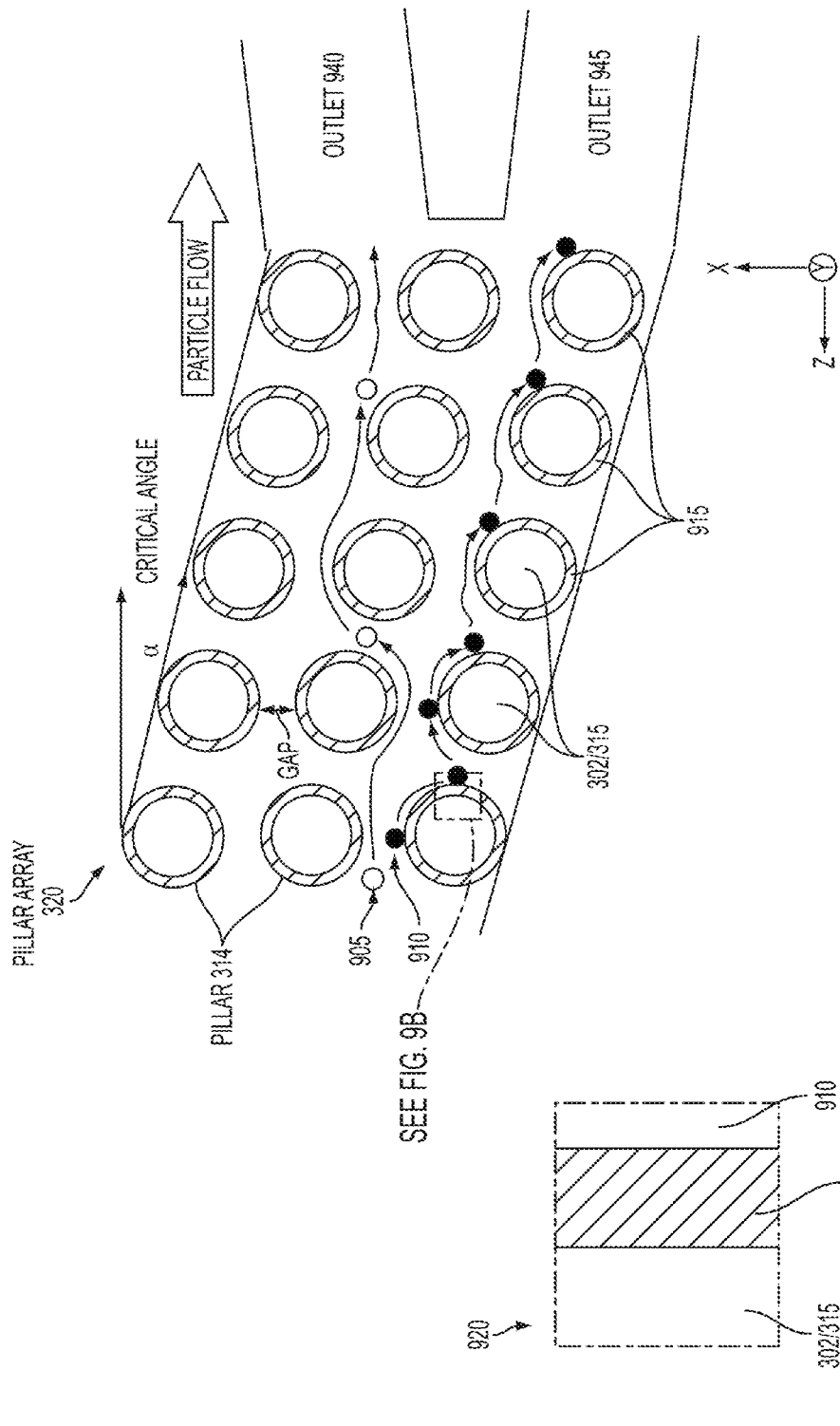

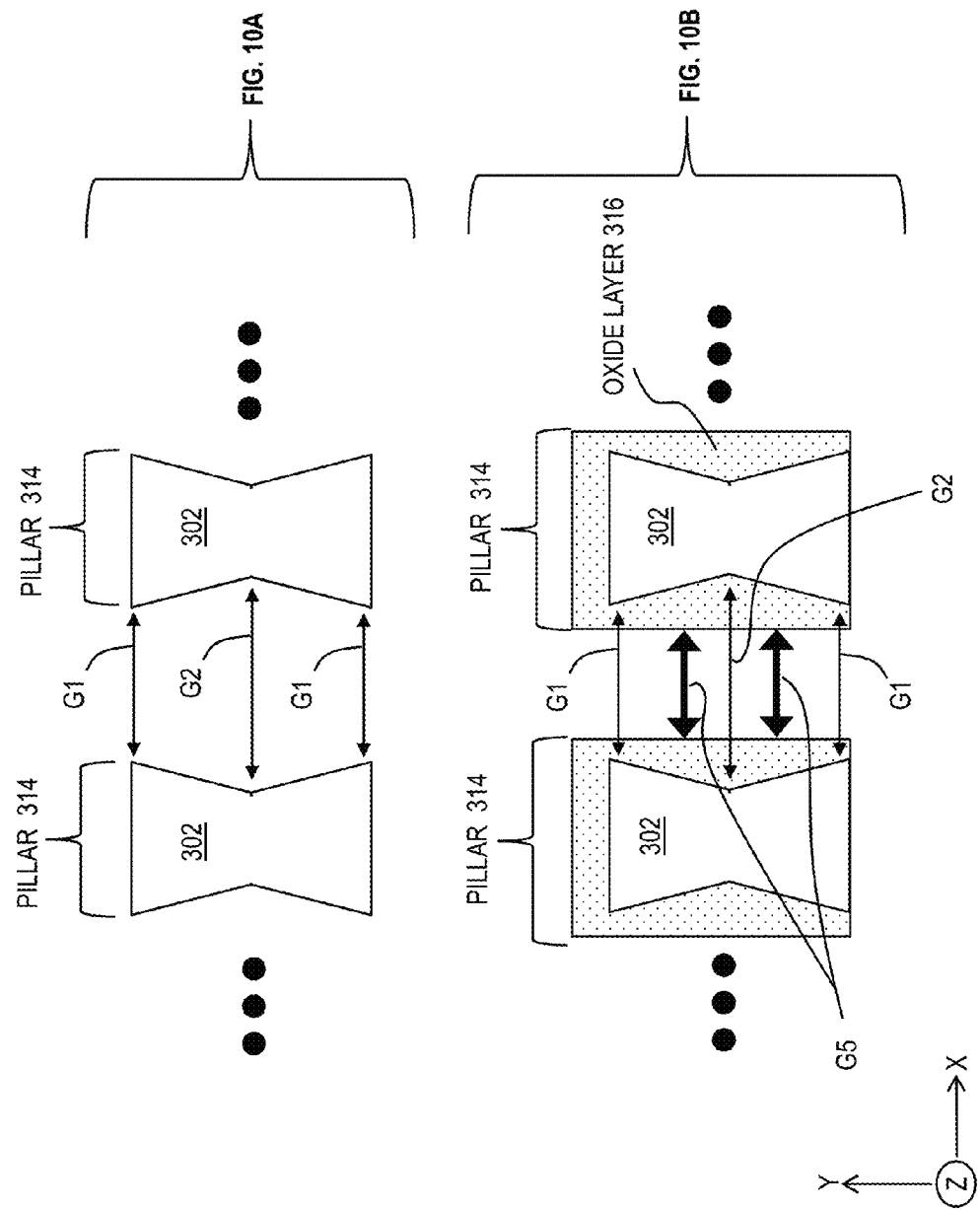

| GAP SIZE VS DIAMETER SIZE | 240nm | 190nm | 120nm | 105nm | 80nm | 60nm | 40nm |
|---|---|---|---|---|---|---|---|
| 110nm | DISPLACEMENT 100% | DISPLACEMENT 100% | N/A | N/A | N/A | N/A | N/A |
| 50nm | NO DISPLACEMENT | PARTIAL DISPLACEMENT | DISPLACEMENT 100% | DISPLACEMENT 100% | DISPLACEMENT 100% | N/A | N/A |
| 20nm | NO DISPLACEMENT | NO DISPLACEMENT | NO DISPLACEMENT | NO DISPLACEMENT | PARTIAL DISPLACEMENT | DISPLACEMENT 100% | DISPLACEMENT 100% |
| 7nm | NO DISPLACEMENT | NO DISPLACEMENT | NO DISPLACEMENT | NO DISPLACEMENT | PARTIAL DISPLACEMENT | PARTIAL DISPLACEMENT | PARTIAL DISPLACEMENT |

INTRODUCE THE ENTITIES INTO A NANOPILLAR ARRAY, THE ENTITIES INCLUDING A FIRST POPULATION AND A SECOND POPULATION, WHERE THE NANOPILLAR ARRAY INCLUDES NANOPILLARS ARRANGED TO HAVE A GAP SEPARATING ONE FROM ANOTHER, AND WHERE THE NANOPILLARS ARE ORDERED TO HAVE AN ARRAY ANGLE RELATIVE TO A FLUID FLOW DIRECTION 1805

SORT THE ENTITIES THROUGH THE NANOPILLAR ARRAY BY TRANSPORTING THE FIRST POPULATION OF THE ENTITIES LESS THAN A PREDETERMINED CRITICAL SIZE IN A FIRST DIRECTION AND BY TRANSPORTING THE SECOND POPULATION OF THE ENTITIES AT LEAST THE PREDETERMINED SIZE IN A SECOND DIRECTION DIFFERENT FROM THE FIRST DIRECTION 1810

THE NANOPILLAR ARRAY IS CONFIGURED TO EMPLOY THE GAP WITH A GAP SIZE LESS THAN ONE OF 300 NANOMETERS OR 100 NANOMETERS IN ORDER TO SORT THE ENTITIES HAVING A SUB-100 NANOMETER SIZE 1815

INTRODUCE ENTITIES INTO A NANOPILLAR ARRAY, THE ENTITIES INCLUDING A FIRST POPULATION AND A SECOND POPULATION, WHERE THE NANOPILLAR ARRAY INCLUDES NANOPILLARS ARRANGED TO HAVE A GAP SEPARATING ONE FROM ANOTHER, AND WHERE THE NANOPILLARS ARE ORDERED TO HAVE AN ARRAY ANGLE RELATIVE TO A FLUID FLOW DIRECTION 1905

RECEIVE THE ENTITIES BASED ON BEING SORTED, SUCH THAT THE FIRST POPULATION OF THE ENTITIES ARE OUTPUT IN A FIRST DIRECTION AND THE SECOND POPULATION OF THE ENTITIES ARE OUTPUT IN A SECOND DIRECTION DIFFERENT FROM THE FIRST DIRECTION 1910

A GAP SIZE OF THE GAP IS TUNED TO SORT THE FIRST POPULATION IN THE FIRST DIRECTION AND THE SECOND POPULATION IN THE SECOND DIRECTION, THE GAP SIZE BEING TUNED ACCORDING TO AT LEAST ONE OF A THICKNESS OF AN OXIDE LAYER DISPOSED ON THE NANOPILLAR ARRAY AND A CHEMICAL MODIFICATION TO THE GAP 1915

FIG. 20

INTRODUCE ENTITIES INTO A NANOPILLAR ARRAY, THE ENTITIES INCLUDING A FIRST POPULATION AND A SECOND POPULATION, WHERE THE NANOPILLAR ARRAY INCLUDES NANOPILLARS IN AN ORDERED ARRANGEMENT, AND WHERE THE NANOPILLARS HAVE A CHEMICAL MODIFICATION 2005

↓

RECEIVE THE ENTITIES AFTER SORTING, SUCH THAT THE FIRST POPULATION OF THE ENTITIES ARE OUTPUT IN A FIRST DIRECTION BASED ON THE FIRST POPULATION HAVING AN AFFINITY TO THE CHEMICAL MODIFICATION AND THE SECOND POPULATION OF THE ENTITIES ARE OUTPUT IN A SECOND DIRECTION DIFFERENT FROM THE FIRST DIRECTION 2010

2000

CONTINUOUS FLOW, SIZE-BASED SEPARATION OF ENTITIES DOWN TO THE NANOMETER SCALE USING NANOPILLAR ARRAYS

DOMESTIC PRIORITY

This application claims priority to U.S. Non-Provisional Application Ser. No. 14/697,072, filed Apr. 27, 2015, which claims benefit to U.S. Provisional Application Ser. No. 62/084,647, filed Nov. 26, 2014, both of which are incorporated herein by reference in their entirety.

BACKGROUND

The present invention relates to a continuous flow size-based separation of entities, and more specifically, to separating entities using a nanopillar array structure.

The separation and sorting of biological entities, such as cells, proteins, deoxyribonucleic acid (DNA), ribonucleic acid (RNA), etc., is important to a vast number of biomedical applications including diagnostics, therapeutics, cell biology, and proteomics.

Protein and DNA/RNA separation for analytical purposes is traditionally done by gel electrophoresis, where a protein mix is subjected to a strong electric field (typically 30 volts per centimeter (V/cm)). Proteins or DNA/RNA move through the gel at a rate depending on their size and surface charge. The gels are prepared from agarose or acrylamide polymers that are known to be toxic. The outcome of the electrophoresis experiment is revealed optically from staining the proteins with dye, or staining the DNA/RNA with ethydium bromide which is extremely carcinogenic. Gels require sufficient quantities of material for the outcome of the electrophoresis to be detectable, but bad cross-linking in the gel matrix often leads to inconclusive results and the complete loss of the samples. If the gel matrix size is not adapted to the sample molecule size or if the electrophoresis is left to run for too long, the sample is also lost.

For separation of macromolecules, such as DNA, RNA, proteins, and their fragments, gel electrophoresis is widely employed. Gel electrophoresis currently has a market with world-wide sales greater than $1 billion dollars per year. Gel electrophoresis applied to medical diagnostic represents a multibillion dollar market.

In comparison with traditional techniques, silicon (Si) nanofabrication technology offers much more precise and accurate control in nano-structural dimensions and positioning of the same, and thus can lead to reliable sorting of particles based on their sizes. To date, Si-based Lab-on-a-Chip approaches using Si pillars arrays have shown promise. However, only sorting in the micron ($10^6$ or micrometer (μm)) range has been demonstrated using these techniques, which does not access the nanometer dimensions required for sorting DNA, proteins, etc.

SUMMARY

According to one embodiment, a method for sorting entities is provided. The entities are introduced into a nanopillar array, and the entities include a first population and a second population. The nanopillar array includes nanopillars arranged to have a gap separating one from another, and the nanopillars are ordered to have an array angle relative to a fluid flow direction. The entities are sorted through the nanopillar array by transporting the first population of the entities less than a predetermined size in a first direction and by transporting the second population of the entities at least the predetermined size in a second direction different from the first direction. The nanopillar array is configured to employ the gap with a gap size less than 300 nanometers in order to sort the entities having a sub-100 nanometer size.

According to one embodiment, a method of sorting is provided. Entities are introduced into a nanopillar array, and the entities include a first population and a second population. The nanopillar array includes nanopillars arranged to have a gap separating one from another, and the nanopillars are ordered to have an array angle relative to a fluid flow direction. The entities are received based on being sorted, such that the first population of the entities is output in a first direction and the second population of the entities is output in a second direction different from the first direction. A gap size of the gap is tuned to sort the first population in the first direction and the second population in the second direction. The gap size is tuned according to at least one of a thickness of an oxide layer disposed on the nanopillar array and/or a chemical modification to the gap.

According to one embodiment, a method of sorting is provided. Entities are introduced into a nanopillar array, and the entities include a first population and a second population. The nanopillar array includes nanopillars in an ordered arrangement, and the nanopillars have a chemical modification. The entities are received after sorting, such that the first population of the entities is output in a first direction based on the first population having an affinity to the chemical modification and the second population of the entities is output in a second direction different from the first direction.

Additional features and advantages are realized through the techniques of the present invention. Other embodiments and aspects of the invention are described in detail herein and are considered a part of the claimed invention. For a better understanding of the invention with the advantages and the features, refer to the description and to the drawings.

BRIEF DESCRIPTION OF THE SEVERAL VIEWS OF THE DRAWINGS

The subject matter which is regarded as the invention is particularly pointed out and distinctly claimed in the claims at the conclusion of the specification. The forgoing and other features, and advantages of the invention are apparent from the following detailed description taken in conjunction with the accompanying drawings in which:

FIG. 3A through 3G illustrate schematics of a process flow for nanopillar array fabrication according to an embodiment, in which:

FIG. 3A illustrates a hard mask layer disposed on a substrate;

FIG. 3B illustrates disposing a resist layer on the hard mask layer;

FIG. 3C illustrates patterning the resist layer;

FIG. 3D illustrates patterning the hard mask layer;

FIG. 3E illustrates etching the substrate into the pillar array;

FIG. 3F illustrates the pillar array with the hard mask pattern removed; and

FIG. 3G illustrates disposing an oxide layer on the pillar array.

FIGS. 5A and 5B are scanning electron microscope images of another wafer to illustrate a fabricated nanopillar array without a thermal oxide according to an embodiment.

FIGS. 5C, 5D, and 5E are scanning electron microscope images of a parallel processed wafer to illustrate the impact of growing a thermal oxide on nanopillar arrays according to an embodiment.

FIGS. 6A and 6B are scanning electron microscope images of another wafer to illustrate starting with a smaller gap size according to an embodiment.

FIGS. 6C and 6D are scanning electron microscope images of a parallel processed wafer to illustrate the oxidation process when the initial gap size is small according to an embodiment.

FIG. 7A illustrates a general chemical schematic of chemical modification to a pillar array to form sorting array surfaces according to an embodiment.

FIG. 7B illustrates a chemical schematic for chemical modification by applying metal to a pillar array to form sorting array surfaces according to an embodiment.

FIGS. 8A through 8D are cross-sectional views illustrating chemical modification of sorting arrays as a means of modifying the gap size between pillars according to an embodiment, in which:

FIG. 8A illustrates the gap size between pillars before chemical modification;

FIG. 8B illustrates the reduced gap size between pillars after chemical modification;

FIG. 8C illustrates an enlarged view of a reactive site in FIG. 8A; and

FIG. 8D illustrates an enlarged view of the monolayer in FIG. 8B.

FIG. 9A is a top view illustrating particle flow in a chemically modified sorting array with particles that have no affinity for the surface monolayer compared to particles that do have affinity for the surface monolayer according to an embodiment.

FIG. 9B is an enlarged view of a cross-section of the nanopillar, monolayer, and particle with affinity according to an embodiment.

FIG. 10A is a cross-sectional view illustrating pillars having gap variation according to an embodiment.

FIG. 10B is a cross-sectional view illustrating the oxidation process that removes the gap variation according to an embodiment.

FIG. 17 is a chart of example data according to an embodiment.

FIG. 18 is a method of sorting entities according to an embodiment.

FIG. 19 is a method of sorting entities according to an embodiment.

FIG. 20 is a method of sorting entities according to an embodiment.

DETAILED DESCRIPTION

Sorting in the micron ($10^6$ μm) range has been demonstrated using Si-based Lab-on-a-Chip approaches. Additional information in this regard is further discussed in a paper entitled "Hydrodynamic Metamaterials: Microfabricated Arrays To Steer, Refract, And Focus Streams Of Biomaterials" by Keith J. Morton, et al., in PNAS 2008 105 (21) 7434-7438 (published ahead of print May 21, 2008), which is herein incorporated by reference.

Figure 1:
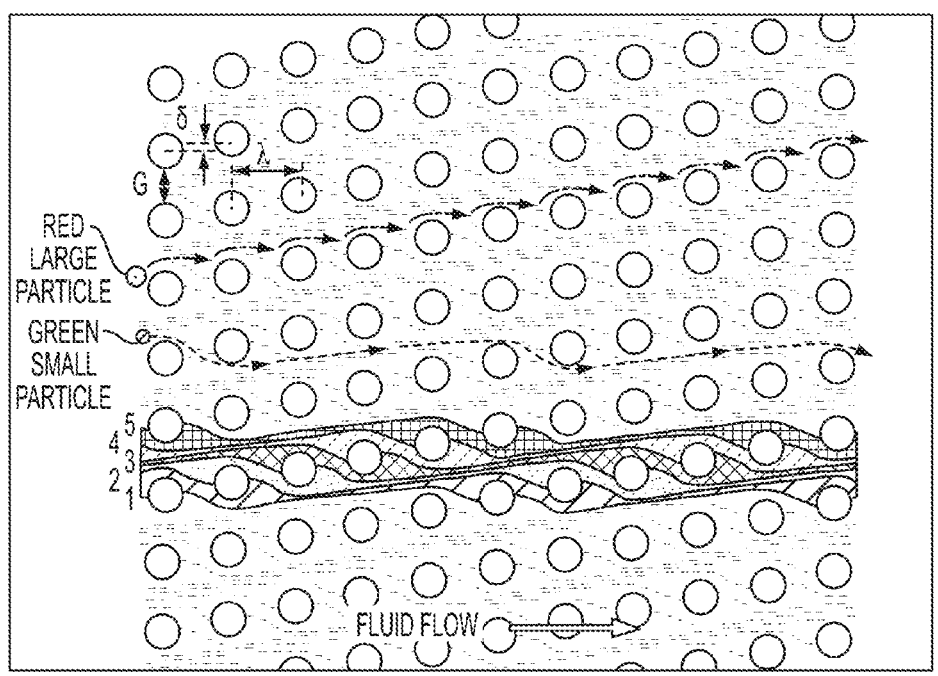
FIG. 1 is a schematic of a deterministic lateral displacement (DLD) array showing definitions of the array parameters.

The paper "Hydrodynamic Metamaterials: Microfabricated Arrays To Steer, Refract, And Focus Streams Of Biomaterials" discusses that their understanding of optics came from viewing light as particles that moved in straight lines and refracted into media in which the speed of light was material-dependent. The paper showed that objects moving through a structured, anisotropic hydrodynamic medium in laminar, high-Peclet-number flow move along trajectories that resemble light rays in optics. One example is the periodic, micro fabricated post array known as the deterministic lateral displacement (DLD) array, a high-resolution microfluidic particle sorter. This post array is asymmetric. Each successive downstream row is shifted relative to the previous row so that the array axis forms an angle α relative to the channel walls and direction of fluid flow as shown in FIG. 1. During operation, particles greater than some critical size are displaced laterally at each row by a post and follow a deterministic path through the array in the so-called "bumping" mode. The trajectory of bumping particles follows the array axis angle α. Particles smaller than the critical size follow the flow streamlines, weaving through the post array in a periodic "zigzag" mode.

FIG. 1 is a schematic of a deterministic lateral displacement (DLD) array showing definitions of the array parameters: The posts are periodically arranged with spacing λ, and each downstream row is offset laterally from the previous row by the amount δ breaking the symmetry of the array. This array axis forms an angle $\alpha=\tan^{-1}(\delta/\lambda)=\tan^{-1}(\epsilon)$ with respect to the channel walls and therefore the direction of fluid flow. Because of the array asymmetry, fluid flow in the gaps between the posts G is partitioned into 1/ε slots. Each of these slots repeats every 1/ε rows so the flow through the array is on average straight. Particles transiting the gap near a post can be displaced into an adjacent streamline (from slot 1 to slot 2) if the particles radius is larger than the slot width in the gap. Therefore, larger particles are deterministically displaced at each post and migrate at an angle α to the flow. Smaller particles simply follow the streamline paths and flow through the array in the direction of fluid flow.

Figure 2A:
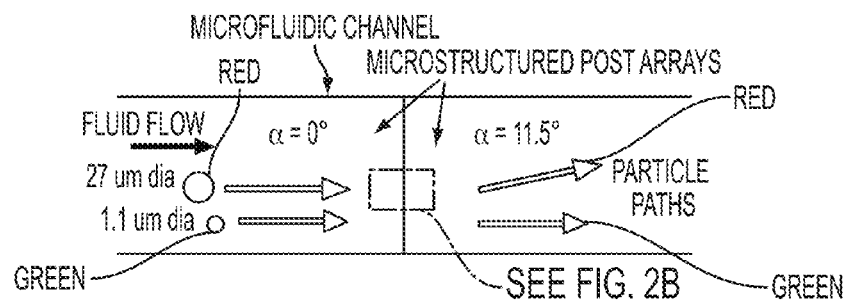
FIG. 2A illustrates a schematic of particle trajectories at the interface between a neutral region and a micro fluidic metamaterial element.
Figure 2B:
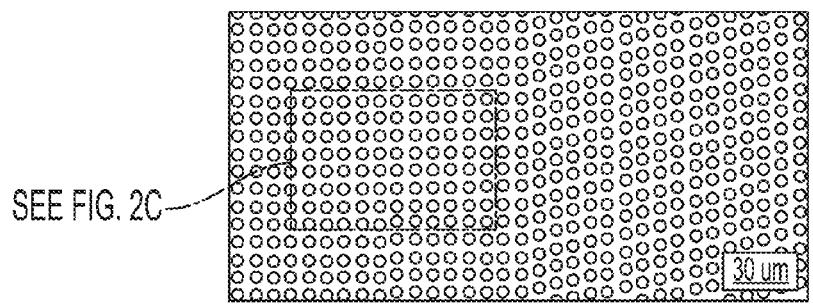
FIG. 2B illustrates the simplest metamaterial element is an asymmetric array of posts tilted at an angle +α relative to the channel walls and bulk fluid flow.
Figure 2C:
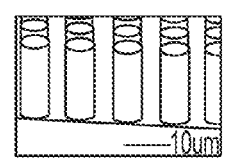
FIG. 2C illustrates a cross-sectional SEM image showing the microfabricated post array.
Figure 2D:
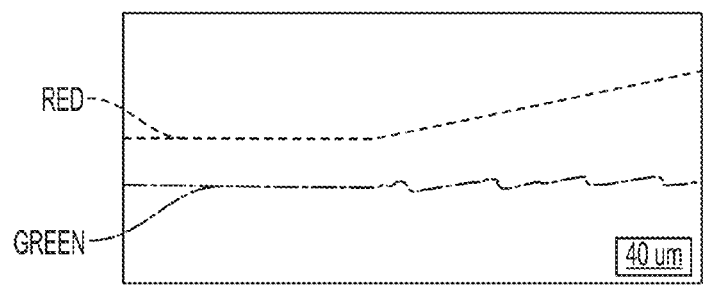
FIG. 2D illustrates equivalent microfluidic birefringence based on particle size showing the time-trace of a 2.7-μm red fluorescent transiting the interface and being deflected from the normal.

FIG. 2A demonstrates size-based birefringence of particles flowing through a hydrodynamic medium of channel-spanning microfabricated posts. Two differently sized particles are normally incident on an interface between a symmetric post array (left half of channel) and an asymmetric post array (right half). Pressure-driven fluid flow through the arrays is from left to right, its overall direction determined by the larger micro fluidic channel. FIG. 2B illustrates a schematic of particle trajectories at the interface between a neutral region and a microfluidic metamaterial element. Particles larger than a critical size follow the array asymmetry, whereas smaller particle follow the fluid flow. FIG. 2B illustrates the simplest metamaterial element is an asymmetric array of posts tilted at an angle +α relative to the channel walls and bulk fluid flow. Shown is a top-view scanning electron micrograph (SEM) of the interface between a neutral array (α=0°) and an array with array angle α=11.3° (the gap G=4 μm and post pitch λ=11 μm are the same for both sides). FIG. 2C illustrates a cross-sectional SEM image showing the microfabricated post array. FIG. 2D illustrates equivalent microfluidic birefringence based on particle size showing the time-trace of a 2.7-μm red fluorescent transiting the interface and being deflected from the normal. Smaller 1.1-μm green beads are not deflected at the interface.

Array elements can be tailored to direct specific particle sizes at an angle to the flow by building arrays with design parameters shown in FIG. 1, which include obstacle size D, spacing between the posts G, and post pitch λ. Asymmetry is determined by the magnitude of the row-to-row shift δ and is characterized by the slope $\epsilon=\delta/\lambda$. The final array angle is then $\alpha=\tan^{-1}(\epsilon)$. For a given array angle, the critical particle size for the bumping mode is determined by the ratio between the particle diameter and the post spacing or gap. This critical particle size has been previously delineated for a range of array angles between 1.0° and 16°. For a given gap size, the critical size of bumping is larger at steeper angles. By using these design criteria, streams of beads, cells, and DNA have all been moved deterministically for size-based separation applications. For the example given in FIG. 1, which has an array angle of 11.3°, gap G=4 μm, and post pitch λ=11 μm, the threshold particle size is ≈2.4 μm. Therefore, 2.7-μm red beads travel along the array axis angle in the bumping mode, and the 1.0-μm green beads travel along streamlines in the zigzag mode, as shown. The array elements and any ancillary microfluidic channels and reservoirs are fabricated in silicon wafers by using standard microfabrication techniques including photolithography and etching. Arrays can also be molded in PDMS by using a similarly crafted silicon master. For the silicon etch, an optimized deep reactive ion etch (DRIE) is used to maintain smooth, vertical side walls, ensuring uniform top-to-bottom spacing between posts as shown in FIG. 2C.

Unlike the state-of-the-art, embodiments are designed to create manufacturable silicon pillar arrays with uniform gaps between the pillars (also referred to as posts) with dimensions in the sub-100 nanometer (nm) regime. These pillar arrays can be used, for example, in a bumper array configuration as described above for the sorting and separation of biological entities at these dimensions, such as DNA, RNA, exosomes, individual proteins, and protein complexes. Particularly, the pillar arrays are designed with an oxide coating, such as a $SiO_2$ coating which can be used to "heal" variation in the gap size along the entire axis of the pillars. Uniform gap sizes are utilized to obtain efficient sorting, e.g., to sort a 20 nm particle from a 10 nm particle. This is particularly challenging for gaps in the sub-100 nm regime where there is inherent variation in gap size greater than the dimensions of the particles to be sorted, which is limited by the reactive-ion etch (RIE) process at this scale. Demonstrated sorting pillar gaps found in the state-of-the-art have dimensions in the micron range, and therefore, the state-of-the-art cannot sort close to this fine of a scale disclosed in embodiments. Even for a pillar array with a very small angle pitch (also referred to as array angle and critical angle), e.g. 0.57 degrees, where sorting efficiency is highest, only a particle greater that 12% of the gap will sort. Therefore, consistent gaps in the nanometer regime are required to sort, for example, a protein aggregate. Sorting of individual proteins (e.g., size range of 1-10 nm) is traditionally performed using ion exchange chromatography or gel electrophoresis, which are load-and-sort techniques rather than a continuous flow Si-based solution. However, the state-of-the-art technique has no existing solution for sorting entities in 10-100 nm scale, but the embodiments provide a solution in both of these ranges (e.g., the 1-10 nm range and the 10-100 nm range). Embodiments also include chemical modification of the pillars via attachment and/or grafting of molecules to further decrease a given gap to a tailored size.

For ease of understanding, sub-headings may be utilized at times. It should be noted that the sub-headings are for explanation purposes only and not limitation.

Pillar Array Fabrication

Figure 3A:
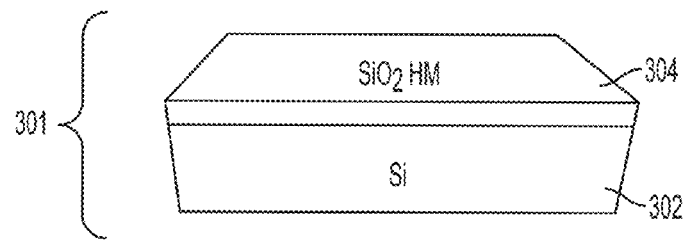

FIGS. 3A through 3G illustrate schematics of a process flow for nanopillar array fabrication according to an embodiment. In FIG. 3A, process flow 301 illustrates a substrate 302. A hard mask 304 is disposed on top of the substrate 302. The substrate 302 may be a wafer, such as, e.g., a silicon (Si) wafer. The oxide hard mask 304 may be silicon dioxide ($SiO_2$) that is used for etching. Although oxide is one example, nitride or another hard material may be utilized. The oxide hard mask 304 may be disposed by deposition and/or growth on bulk silicon (substrate 302). The thickness of the oxide hard mask 304 may range from tens to several hundred nanometers, depending on the etch depth needed to create the height of the pillars and the selectivity of the RIE chemistry for the substrate 302 versus the hard mask material 304. Other materials may be utilized for the substrate 302 and the hard mask layer 304.

Figure 3B:
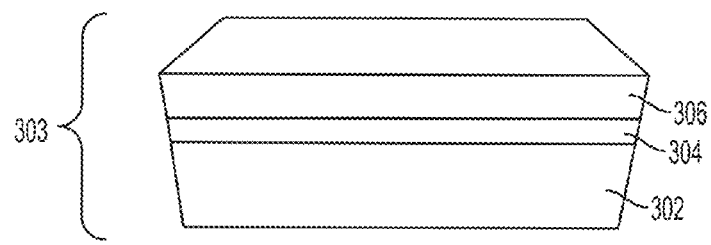

In FIG. 3B, process flow 303 illustrates disposing a resist 306 on top of the oxide hard mask 304. The resist 306 may be a positive resist or a negative resist. The thickness of the resist 306 may range from 100 nm-1 μm, depending on the resist 306, hard mark (304) etch selectivity, the thickness of the hard mask 304, and nanopillar gap resolution needed. For narrow sub-100 nm gaps and shallow pillar depths, a resist thickness range of 100-500 nm is utilized to achieve higher resolution features with less variability in gap size. The resist 306 may also be a multi-layer resist stack comprised of two or more layers each with different etch selectivity to improve resolution.

Figure 3C:
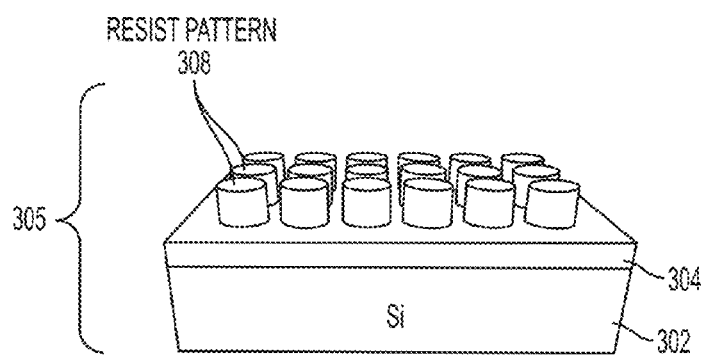

In FIG. 3C, process flow 305 illustrates patterning the resist 306 into a resist pattern 308. The resist pattern 308 may be defined but is not limited to using electron-beam lithography, nanoimprint lithography, interference lithography, extreme ultraviolet lithography, and/or deep ultraviolet lithography or a combination of these techniques. The resist pattern 308 is formed into resist pillars in the pattern of the future nanopillar array. In one case, the resist pattern 308 may include multiple patterns for different nanopillar arrays.

Figure 3D:
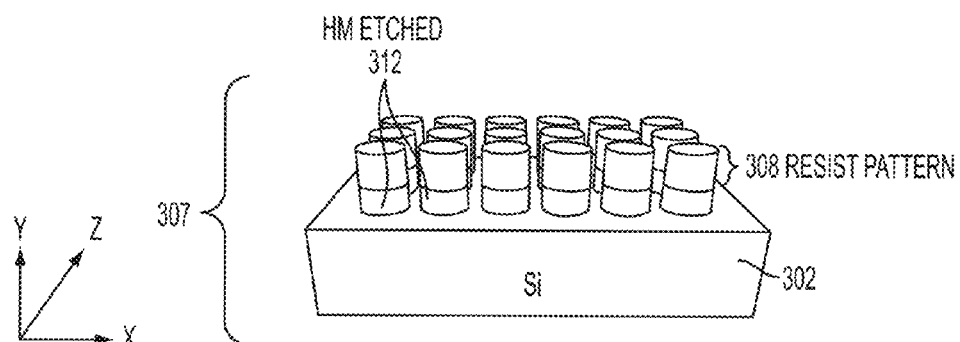

Process flow 307 illustrates pattern transfer from the resist pattern 308 to the oxide hard mask 304 to result in the etched hard mask pattern 312 in FIG. 3D. The pattern transfer to the hard mask 304 may be performed using reactive ion etching (RIE). Process flow 307 shows the resist pattern 308 on top of the corresponding etched hard mask pattern 312.

Figure 3E:
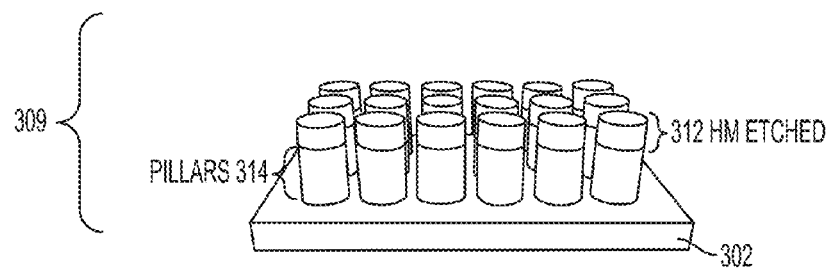

In FIG. 3E, process flow 309 illustrates patterning the nanopillars 314 to be defined in the substrate 302 underneath the etched hard mask pattern 312. The nanopillars 314 may be etched using reactive ion etching. The resist pattern 308 may be removed from on top of the etched hard mask pattern 312 before patterning the nanopillars 314 in the substrate 302 or after patterning the nanopillars 314. Removing the resist pattern 308 after etching the nanopillars 314 may be performed as it can serve to avoid hard mask pattern 312 erosion that can occur during the nanopillar 314 RIE process. Hard mask erosion, in turn, may lead to pillars with a tampered (undesired) sidewall angle.

Figure 3F:
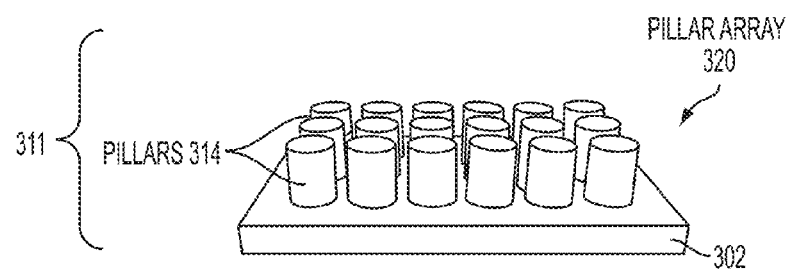

Process flow 311 illustrates removal of the hard mask pattern 312 in FIG. 3F. The hard mask pattern 312 may be removed in dilute hydrofluoric (DHF) acid, if the hard mask material is $SiO_2$. Process flow 311 shows a nanopillar array 320 of nanopillars 314.

Figure 3G:
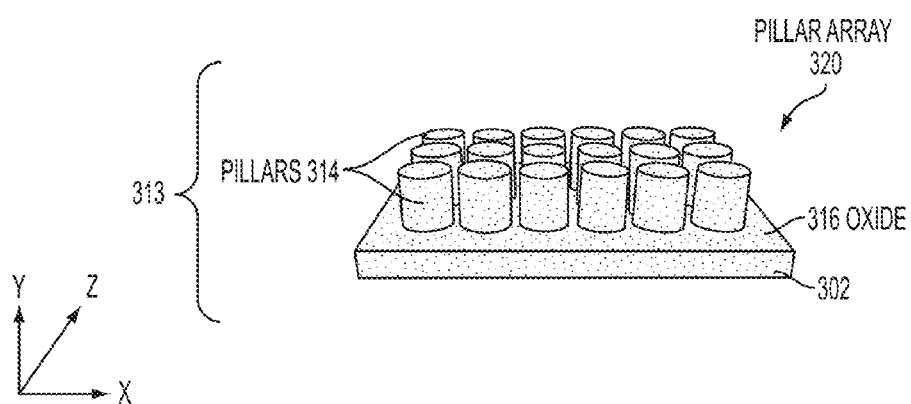

To further reduce the size of gaps between each of the nanopillars 314 and to reduce gap variation, process flow 313 illustrates disposing oxide 316 to cover the surface of the nanopillar array 320 formed in the substrate 302 in FIG. 3G. In one case, thermal oxidation may be utilized to grow silicon dioxide 316 to cover of the surface of the nanopillar array 320 in order to narrow the gaps. In another case, the oxide 316 may be deposited on the nanopillar array 320 (made of silicon), for example using atomic layer deposition.

In general, pillar arrays include a dense array of silicon pillars defined by RIE followed by an oxidation operation (e.g., process flow 313) that serves to narrow the gaps between the pillar posts and minimize gap variation. Nanopillar array fabrication may also include an optional chemical modification operation where further gap scaling (i.e., reduction in size) may be required. These pillar and/or gap arrays can be implemented into angled pillar designs to concentrate a sample or separate a heterogeneous mixture of biological entities at the single molecule level, similar to work demonstrated by the paper "Hydrodynamic Metamaterials: Microfabricated Arrays To Steer, Refract, And Focus Streams Of Biomaterials" for cell or large particle sorting. The process flow for nanopillar array fabrication in FIGS. 3A and 3B can be utilized to create arrays of nanopillars 314 shifted in any desired gap G spacing between the nanopillars 314, desired pillar pitch $\lambda$, desired row-to-row shift $\delta$, and desired array angle $\alpha$ (also referred to as the critical angle $\alpha$) (as shown in FIG. 1).

Multiple nanopillar arrays 320 (e.g., 1-N, where N is the last number of nanopillar arrays 320) may be fabricated as discussed in FIGS. 3A and 3B on the same substrate 302. The first nanopillar arrays 320 may have a first set of parameters (desired gap G spacing between the nanopillars 314, desired pillar pitch $\lambda$, desired row-to-row shift $\delta$, and desired array angle $\alpha$). The second nanopillar arrays 320 may have a second set of parameters (desired gap G spacing between the nanopillars 314, desired pillar pitch $\lambda$, desired row-to-row shift $\delta$, and desired array angle $\alpha$), where one or more of the first set of parameters can be different from the second set of parameters. The third nanopillar arrays 320 may have a third set of parameters (desired gap G spacing between the nanopillars 314, desired pillar pitch $\lambda$, desired row-to-row shift $\delta$, and desired array angle $\alpha$), where one or more of the first set of parameters can be different from and/or the same as some of the second set of parameters, and one or more of the third set of parameters can be different from and/or the same as some of the first and second set of parameters. This same analogy can apply through the last (N) nanopillar arrays 320 which may have a last (N) set of parameters (desired gap G spacing between the nanopillars 314, desired pillar pitch $\lambda$, desired row-to-row shift $\delta$, and desired array angle $\alpha$), where one or more of the last set of parameters can be different from and/or the same as any one of first, second, third, and N−1 set of parameters.

To define the pillars and gaps, a negative-tone nanoscale lithography technique may be better to ensure a patterned gap size less than (<) 100 nm to begin with, e.g., the pillars and gaps are defined in the resist pattern 308 shown in process flow 305. Electron-beam lithography is one option where pillars array patterns are smaller. However, the more manufacturable approach of nanoimprint lithography can also be applied as well as extreme ultraviolet (EUV) and deep ultraviolet (DUV) lithography under well controlled dose conditions. To achieve a high aspect ratio pillars, the written pattern (i.e., resist pattern 308) must be transferred to the hard mask 304 (hard mask pattern 312) before etching the (Si) substrate 302. High aspect ratio pillars permit larger fluidic throughput and can reduce clogging issues associated with micro/nanofluidic features. High aspect ratio pillars are therefore a useful feature to have so long as the gap size can be maintained between adjacent pillars. By defining the pillars in the resist pattern 308 and transferring them to the etched hard mask pattern 312 first, the benefit of etch selectivity increases the aspect ratio while maintaining a more consistent gap size when the pillar array (320) etch is performed.

Some experimental data is discussed below as example implementations. The experimental data is for explanation and not limitation. In this case, electron-beam lithography was utilized to define the pillar dimensions (e.g., resist pattern 308) in hydrogen silsesquioxane (HSQ) as part of a double layer resist stack (e.g., resist 306), which is then transferred to a 150 nm undensified low-temperature oxide (LTO) hard mask (e.g., etched hard mask pattern 312). Densified LTO, thermal oxide and/or $SiO_2/SiN/SiO_2$ hard masks may also be considered. The experiment then used a RIE-based Si etch process to define the pillars (e.g., pillars 314) in the substrate. Further details of the RIE process are now described.

RIE Process Details: Dry etching was carried out in an Applied Materials DPSII ICP etch chamber for pattern transfer to fabricate 400 nm high Si pillars from the e-beam resist pattern. First, the developed negative tone e-beam resist (HSQ) is used to etch through an organic planarization layer (OPL) mask using a $N_2/O_2/Ar/C_2H_4$ chemistry at 400 watts (W) source power, 100 W bias power, and 4 millitorr (mTorr) pressure at 65° C. Then, the pattern is transferred further into a $SiO_2$ hard mask using $CF_4/CHF_3$ chemistry at 500 W source power, 100 W bias power, and 30 mTorr pressure at 65° C. The carbon hard mask is then stripped using O$_2$/N$_2$ chemistry in an Applied Materials Axiom downstream asher at 250° C. Using the SiO$_2$ hard mask, Si pillars are etched to 400 nm depth using the DPS II by first a CF$_4$/C$_2$H$_4$ breakthrough step and then Cl$_2$/HBr/CF$_4$/He/ O$_2$/C$_2$H$_4$ main etch at 650 W source power, 85 W bias power and 4 mTorr pressure at 65° C. It is noted that three masks were utilized to eventually etch the pillars, and the three masks were the developed HSQ e-beam resist (mask), the OPL mask, and the SiO$_2$ hard mask.

Gap Analysis

Figure 4A:
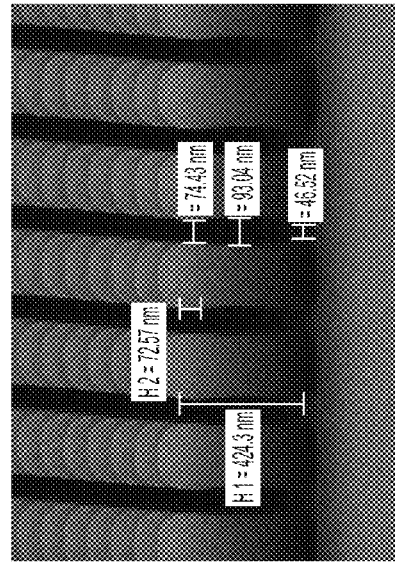
FIGS. 4A and 4B are scanning electron microscope images of the same wafer to illustrate the result of reactive ion etching before hard masks are removed according to an embodiment.
Figure 4B:
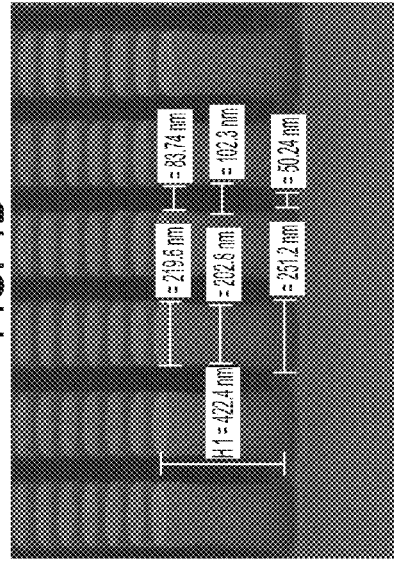
Figure 4C:
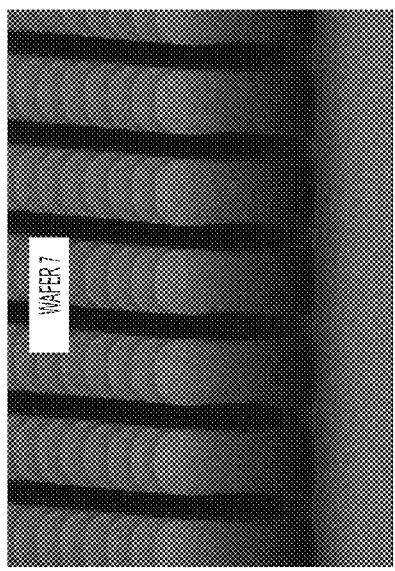
FIGS. 4C and 4D are scanning electron microscope images of a parallel processed wafer to illustrate the result of reactive ion etching after hard masks are removed according to an embodiment.
Figure 4D:
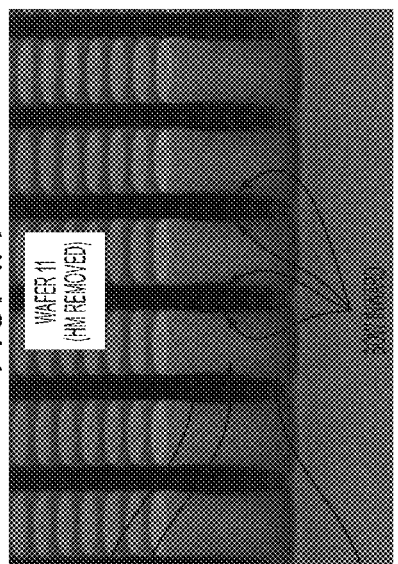

FIGS. 4A, 4B, 4C, and 4D are scanning electron microscope images of the result of this RIE process for two separate instances. FIGS. 4A and 4B illustrate the pillars (e.g., pillars 314) before the hard mask (e.g., hard mask pattern 312) is removed (such as in process flow 309), and the tops of the pillars (pillars 314 with hard mask pattern 312 on top) have a rounded shape. The 150 nm LTO (undensified) hard mask was utilized together with a RIE etch to produce the pillars 314 in FIGS. 4A and 4B. FIGS. 4C and 4D illustrate pillars (e.g., pillars 314) after hard mask (e.g., hard mask pattern 312) removal by dilute hydrofluoric acid carried out on different wafers, and the tops of the pillars 314 are flat in FIGS. 4C and 4D. In both cases, the Si pillars bow inward at the center due to the high density of the pillars in the array. That is, the gaps between pillars widen at the center of the pillars 314 because the diameter of the pillars are reduced at the center. The pillars have an inward-bowed shape or an hour glass shape. It is noted that pillars at the boundaries of the array are very vertical (not shown). This highlights the problem of gap non-uniformity at the nanometer scale where approximately (~) 100 nm gap sizes have approximately 50 nm of gap variation from the top of a pillar to bottom (i.e., depth or height) of the same pillar as seen in FIGS. 4C and 4D. The close proximity of pillars in the array as defined by the gap caused the pillars to bow inward at the center, producing gap variation that inhibits further scaling. This effect has been observed on gap sizes with dimensions of 250 nm and below for the etch process described above (i.e., prior to disposing the oxide layer 316).

According to an embodiment, FIGS. 5A and 5B are scanning electron microscope images of the fabricated nanopillar array of wafer 5 without a 50 nm thick thermal oxide. FIGS. 5C, 5D, and 5E are scanning electron microscope images of wafer 7 showing the impact of growing a 50 nm thick thermal oxide (e.g., oxide layer 316) on nanopillar arrays embedded in Si according to an embodiment. On the side of the pillars, there is a right wall 505 (shown in FIGS. 5A and 5C), a bottom 510 of the substrate, and a left wall 515 (shown in FIG. 5B).

The processing of pillars in FIGS. 5A and 5B for wafer 5 are identical to the processing of pillars on wafer 7 in FIGS. 5C, 5D, and 5E except for the final oxidation step (only performed on wafer 7 in FIGS. 5C-5E). In the case of FIG. 5B (wafer 5), there is 26 nm of variation for the gap size of approximately 186 nm while FIG. 5D (wafer 7) shows only a 13 nm variation in gap size after oxidation with the gap size narrowing to approximately 138 nm in this case. This healing effect of oxidation occurs as a result of oxide non-uniformity on these non-planar structures (i.e., pillars) as shown in FIG. 5E. FIG. 5E shows that relative to two pillars (from a side-by-side perspective in the x-axis), the gap size between those two pillars can only vary by 13 nm from top to bottom (i.e., along the vertical axis of the y-axis) because the oxide has filled in the inward-bowed shape. Using the etch process applied to FIGS. 5A and 5B (wafer 5), uneven oxidation on pillar features is found to "heal" gap variation as shown in FIGS. 5C, 5D, 5E (wafer 7) as the oxidation proceeds more rapidly at the center of the pillars (instead of at the top and bottom), and this is shown further in FIGS. 10A and 10B.

FIGS. 6A and 6B (wafer 5) illustrate starting with a smaller gap size such as 80-89 nm (varies by 9 nm) in which no oxide is disposed to fill in the hour glass shape. FIGS. 6C and 6D (wafer 7) illustrate the 50 nm oxidation step applied when the original gap size is 80-89 nm (varies by 9 nm). The impact of oxidation is very apparent in FIGS. 6C and 6D where the same 50 nm oxidation step (discussed above in FIGS. 5C, 5D, 5E) reduces the gap size from 80-89 nm to just 21-25 nm (gap variation 4 nm) with a 12:1 (depth:gap) ratio. As seen in FIGS. 6C and 6D, oxidation on smaller starting gap sizes (e.g., such as 80-89 nm (or smaller) before the oxidation step to narrow the gap and remove the inward-bow) yields approximately 25 nm gaps with only a few nanometers variation (4 nm) over approximately a 300 nm etch depth, where the depth to gap ratio of 300:25 results in the 12:1 ratio. This small amount of gap variation (e.g., 4 nm) and process opens up the opportunity to make custom, tunable gap sizes, particularly when these nanopillars are combined with chemical modification processes. The term high aspect ratio can pertain to structures with a depth to gap ratio of greater than 4:1, which can be difficult to achieve at this scale in a manufacturable process.

By disposing the oxide on the pillar array as discussed herein, embodiments are configured to provide a pillar array with a gap size that is uniform along the vertical axis (i.e., the depth) of two pillars that are side-by-side (e.g., the gap size between the two side-by-side pillars varies less than 5 nm (such as by 4 nm, 3 nm, 2 nm)). For example, FIGS. 10A and 10B are cross-sectional views illustrating the healing process that removes (reduces) the gap variation and creates a uniform gap size in the pillar array 320 according to an embodiment. For illustration purposes only, two pillars 314 are shown side-by-side but the illustration applies to all of the pillars 314 in the pillar array 320. The height of the pillars 314 is shown on the y-axis, and the width/diameter is shown on the x-axis. The z-axis represent to length of the array 320, and additional pillars 314 (not shown) in the array are positioned in front of and behind the two pillars 314. FIG. 10A shows two example pillars 314 made out of their substrate material (substrate 302). The pillars 314 are bowed inward to have an hour glass shape. In FIG. 10A, two gap sizes G1 and G2 are shown but there may be additional gap sizes between gap sizes G1 and G2. The gap size G1 is at (near) the top and bottom of the pillars 314. The gap size G2 is at (near) the center of the pillars 314. The close proximity of pillars 314 as defined by the gap size G1 in the array 320 may cause the hour glass shape because of the dimensional constraints of the gap size G1 imposed on the impinging flux of reactive ions during the RIE process.

FIG. 10B shows the two example pillars 314 after disposing the oxide layer 316. Because of the non-planar architecture, nanosize of the pillars, and the tight nano-spacing between the pillars 314 in the pillar array 320, the oxide layer 316 does not distribute evenly on the pillars 314. Instead, more oxide 316 is formed more rapidly in the center (cavities) of the pillars 314 than at the top and bottom of the pillars 314 in the y-axis. In other words, the bowed-in centers are filled in at a faster rate than the tops and bottoms of the pillars 314. This uneven distribution of the oxide 316 formed on the pillars 314 serves to straighten the individual pillars 314 changing them from the hour glass shape to a cylinder-like shape, which in turn makes the gap size G5 uniform between the two pillars 314 (and any other two pillars 314 side-by-side in the x-axis). Accordingly, all of the gaps G (representing the general gap size of the array) are uniform throughout the pillar array 320.

Chemical Modification

Interaction between the particles to be sorted and the surfaces of the array can be tailored by using chemical modification. In general, this can involve the attachment and/or grafting of molecules to the surfaces of the pillar array, through physical adsorption and/or formation of chemical bonds. Also, the chemical modification of the pillar array can include application of a layer(s) of material such as a metal, polymer, and/or ceramic coating, as well as changes to the oxidation state of the array surface. Surfaces (for chemical modification) can include the areas of the sorting pillars, the walls, the ceiling, and/or the floors of the fluidic pillar array. Additionally, chemical modification can be on any surfaces present in the inlets, outlets, drive mechanisms, and/or other fluidic channels attached to the nanofluidic device (e.g., one or more pillar arrays).

Although the chemical modification can be applied as discussed above, the better application is the chemical modification of the sorting pillars themselves, as this allows design of the interactions between the particles with the sorting array surfaces.

In one example, a small organic molecule or polymer, termed a ligand, can be chemically grafted to the surface of the pillars, such as through condensation of chlorosilane and/or alkoxysilanes on the pillars' native silicon oxide as illustrated in FIG. 7A. Also, the ligand can be chemically grafted to the surface of the pillars, such as through thiols, amines, and/or phosphines on pillars coated with a thin layer (e.g., 10 nm) of gold or silver as illustrated in FIG. 7B. The resulting layer of ligand molecules is a single molecule thick, i.e., a monolayer. The terminal groups of the monolayer, which are in direct contact with the fluid and particles, determine the physochemical interactions felt by the particles as they pass through the array. Changing the terminal group of the ligand therefore allows tailoring of the surface interactions within the array.

FIGS. 7A and 7B illustrate the general chemical schematic of methods of chemical modification of sorting array surfaces according to an embodiment. Referring to FIG. 7A, for a generic substrate (array pillar) reactive sites (X) on the surface can be used to form chemical bonds and/or physical absorption of small molecule ligands. The attachment of ligands to the surface forms a new layer, which is a single molecule thick (i.e., the monolayer). A general ligand consists of (i) a bonding group (Z) which interacts with the substrate reactive site (X), (ii) a backbone which consists of a number of spacer molecules (n) that determine in-large the thickness of the final monolayer, and (iii) a terminal group (A) which interacts with the interface between the monolayer and the fluid/particles in the array. The terminal group (A) interacts with the particles to be sorted. Although FIG. 7A shows the bonding group Z and reactive site X, this is just one example and the chemical modification is not meant to be limited to the one type of reaction mechanism in this example. There are two other general mechanistic possibilities: (1) direct bond formation, i.e. the Z group bonds to the reactive site X in a Z—X bond, and/or (2) bond formation with elimination, i.e. the reactive group Z—W bonds to the reactive site X—V in a Z—X bond, with the byproducts W, V eliminated. For example, the reaction of chlorosilanes R—Si—Cl with a silanol on the silica surface, H—O—Si, forms the R—Si—O—Si bond with the elimination of HCl.

Referring to FIG. 7B, monolayers can be formed on metal layers (M) pre-eposited onto the array of pillars. For example, one or more metal layers (M) can be deposited on the pillars (e.g., after the oxidization process that creates the uniform gap size), such that the pillars now have a metal surface (M) over the substrate (and/or over the oxide layer that fills in the inward bow). In FIG. 7B, the bonding group is identified with 'Q' as opposed to 'Z' in FIG. 7A. Ligands (e.g., with the bonding group (Q)) can form coordination complexes directly with the metal surface (M) of the pillar array, forming a tightly packed monolayer.

Chemical modification can be used to tune the pillar array to sort smaller particles by decreasing the gap size as illustrated in FIGS. 8A and 8B. The surfaces of the sorting pillars 314 can be modified with molecules of various length, including aliphatic or aromatic oligomers/polymers, which effectively increase the thickness of the pillars and thereby reduce the gap space between them. By selecting longer ligands, the gap size can be made smaller and therefore the effective cut-off particle size lowered (i.e., smaller particles can be sorted). The backbone of the ligand can be selected to provide a range of mechanical properties between either a rigid, tight packed molecular layer and/or a flexible, disordered layer. Ligands can include small organic molecules, proteins, peptides, nucleic acids, oligosaccharides, and/or synthetic polymers. In one example, pillar surfaces are modified with oligomers of polyethylene glycol (PEG) through siloxane linkages. At approximately 0.36 nm per ethylene oxide residue, for a 12 residue PEG oligomer, this produces an approximately 9 nm decrease in the gap size; for a 20 residue PEG oligomer this is approximately a 14 nm decrease in the gap size.

FIGS. 8A through 8D illustrate schematics of chemical modification of sorting arrays as a means of modifying the gap size between pillars according to an embodiment. Referring to FIG. 8A, for pillars 314 with their native oxide, a grown oxide layer, and/or a deposited layer of alternative material, e.g. metal, ceramic, polymer, there are reactive sites (X) on the surface of the pillars. The pillars 314 have an initial gap width denoted by g. There is an array floor 805 (which is the floor of the substrate 302 on which the pillars stand). FIG. 8C shows an enlarged view 820 that depicts the empty reactive site (X) in FIG. 8A. In view 820, the reactive site (X) is not attached to a ligand, but the ligand is to be applied to the pillar array 320 as shown in FIG. 8B.

Referring to FIG. 8B, chemical attachment of the ligand 810 to the pillars' surfaces forms a monolayer 815 which has a thickness determined by the properties of the ligand packing. The added thickness of the monolayer 815 reduces the gap width (from initial gap width g) to a new effective gap width ($g_e$). Adjustment of the ligand structure, in particular the backbone, as well as the packing and defect density of the monolayer 815, can tailor the thickness of the monolayer 815 and thus the tailor the effective gap ($g_e$). The effective gap ($g_e$) is the new physical gap size experienced by the particles as they flow through the array 320, and is formed from the combination of the physical barrier of the pillars plus the added steric barrier of the monolayer. The effective gap is, in general, an approximate value, dependent on the structural, mechanical, and dynamic properties of the monolayer under the operation conditions of the particle sorting. FIG. 8D shows an enlarged view 820 in which the reactive sites (X) have been attached to the ligands 810, thereby extending the diameter of the pillars 314.

Further improvement and refining of the sorting array can be introduced through the terminal group(s) (A) of the ligands, which can be selected to have specific interactions with the fluid and/or particles to be sorted as shown in the schematic of FIG. 9. When the particles flow through the pillar array 320, interactions with the terminal groups of the monolayer 915 leads to increased adhesion and temporary retention on the pillar walls of pillars 314. These interactions slow down the particle's flow, as well as causes the particles, on average, to be positioned more at the walls of the pillars, therefore reducing the amount of the flow field it samples. As the pitch of the array is asymmetric with respect to the average fluid flow, particles (such as particles 910) that retain and transition between pillars 314 are effectively moved along the critical angle of the array and are sorted out. In one example, thiol terminal groups at the end of PEG-type ligands can be used to formed disulfide linkages between transiting particles such as proteins or other molecules labeled with thiols. In combination with a suitable catalyst agent in the fluid, when proteins (such as particles 910) flow through the array 320 they can form disulfide bonds with the pillars 314, temporarily arresting their flow. In another example, small segments of a chemically stable nucleic acid such as peptide nucleic acid (PNA) can be attached to the pillar walls, to selectively delay and sort out DNA or RNA analytes through reversible base pairing. In another example, patches of hydrophobic ligands embedded within hydrophilic monolayers can be introduced onto pillars, one such pair being aliphatic hydrocarbon ligands and PEG. The hydrophobic patches can be used to interact with hydrophobic domains on proteins, to selectively sort them from solution.

FIG. 9A provides illustration of particle flow in chemically modified sorting array with particles 905 that have no affinity for the surface monolayer 915 and particles 910 which interact with the monolayer 915. Particles 905 with no affinity follow the flow lines through the array 320 (i.e., exhibit a zigzag mode) and are not subject to any strong interactions with the pillars 314. The trajectory of these particles 905 is unaffected on average, and they flow without sorting in the array 320. For example, the particles 905 flow into an outlet 940. However, particles 910 with a physo-chemical affinity, caused by molecules on their surface, experience interactions with the molecules of monolayer 915 on the surface of the pillars 314. The interactions can temporarily bind these particles 910 to the surface of the pillars 314, and cause particles 910 to, on average, remain closer to the pillar walls of the pillars 314. Through several sequential binding and dissociation events, the particles 910 are transferred along the direction of the pillars 314 (i.e., exhibit a bump mode in the direction of the critical angle α) and are sorted by the array 320 due to chemical affinity. The particles 910 are sorted into an outlet 945. FIG. 9B is an enlarged view of a cross-section of the nanopillar 314, monolayer 915, and particle 910 with affinity according to an embodiment.

To chemically modify the pillar array 320, the ligand can be introduced through chemical vapor deposition (CVD) and/or wet chemistry. To apply the metal, CVD, sputtering, and/or wet chemistry may be utilized. Two detailed examples of chemically modifying the pillars 314 by adding a monolayer discussed for explanation purposes and not limitation, and the two examples using wet chemistry are provided below.

For illustration purposes, an example method of modification of a microfluidic device using poly(ethyleneoxide) (PEG) ligand modifiers is provided below: All glassware to be exposed to chlorosilanes, is first washed in an isopropanol bath saturated with potassium hydroxide for at least 24 hours, then rinsed thoroughly with deionized water and dried in an oven at 140° C. for 12 hours.

A 100 mL round bottom flask is removed from the 140° C. oven and quickly sealed with a septum. A nitrogen gas purge is set up through the septum using needles, and the flask allowed to purge for 10 minutes. 30 mL of anhydrous toluene is transferred into the flask via cannula. Via syringe, 600 μL of n-octyldecyltrichlorosilane is injected to form a 49 mM solution. The flask is momentarily vortexed to mix the reagents homogenously. This forms the passivation solution. A 500 mL reactor and 3-neck head are removed from the 140° C. oven and then quickly sealed together, with each inlet closed with a septum. A nitrogen gas purge is set up through the septum using needles, and the flask allowed to purge for 10 minutes. Via cannula, 20 mL of the passivation solution in the 100 mL flask is transferred to the reactor. The reactor is gently shaken to swish the passivation solution around the walls of the reactor thoroughly. The same is done for the 100 mL flask using the remaining passivation solution. This gentle shaking is repeated every 10-15 minutes, for 1 hr. Between shaking, the glassware is allow to sit at ambient temperature. This procedure is to passivate the walls of the glassware against further silizanizaiton. The passivation solution is then poured out of the reactor, and the reactor washed sequentially, 3× each, with toluene, acetone, isopropanol and deionized water. The same is done for the 100 mL flask. The glassware is then returned to the 140° C. oven and allowed to dry 12-14 hours.

The 100 mL round bottom flask is removed from the 140° C. oven and quickly sealed with a septum. A nitrogen gas purge is set up through the septum using needles, and the flask allowed to purge for 30 min. 100 mL of anhydrous toluene is transferred into the flask via cannula. Via syringe, 100 μL of 2-(methoxypoly(ethyleneoxy)$_{6-9}$propyl) dimethylchlorosilane is injected to form an approximately 2 mM solution. The flask is momentarily vortexed to mix the reagents homogenously. This modification solution is used within the day of its preparation.

Silica/silicon based microfluidic devices (chips) are cleaned for 30 min in an oxygen plasma to remove organic surface contamination. The chips are transferred then to a 0.1M aqueous nitric acid solution for 10 min to hydrolyze any surface siloxane bonds to silanols. The chips are then washed sequentially, using a squeeze bottle stream, in deionized water, acetone, ethanol, and then isopropanol. The chip is then set face-up on a fresh texwipe and immediately dried off using a stream of nitrogen gas, pushing solvent from the middle to outside of the chip. The chips are then set on a custom glass holder (which sets the chips horizontal/face-up inside the reactor, as described below).

A 500 mL reactor and 3-neck head are removed from the 140° C. oven. A stir bead along with the glass holder and chips are set into the reactor, and then quickly sealed together, with each inlet closed with a septum. A nitrogen gas purge is set up through the septum using needles, and the reactor allowed to purge for 30 minutes.

Via a cannula, the modification solution (with the ligand) is transferred into the reaction flask until the solution level is above the chips. Nitrogen positive pressure is then maintained using a bubbler. The reaction is allowed to run for 2 hours, at ambient temperature, with stirring. The reactor is then opened and the chips cleaned (one-by-one) by rinsing sequentially, using a squeeze bottle stream, toluene, acetone, isopropanol, then deionized water. The chip is then set face-up on a fresh texwipe and immediately dried off using a stream of nitrogen gas, pushing solvent from the middle to outside of the chip. The chips are then set in a glass holding jar with a septum. A nitrogen gas purge is set up through the septum using needles, and the chips allowed to dry overnight (approximately 12-14 hours).

Figure 11:
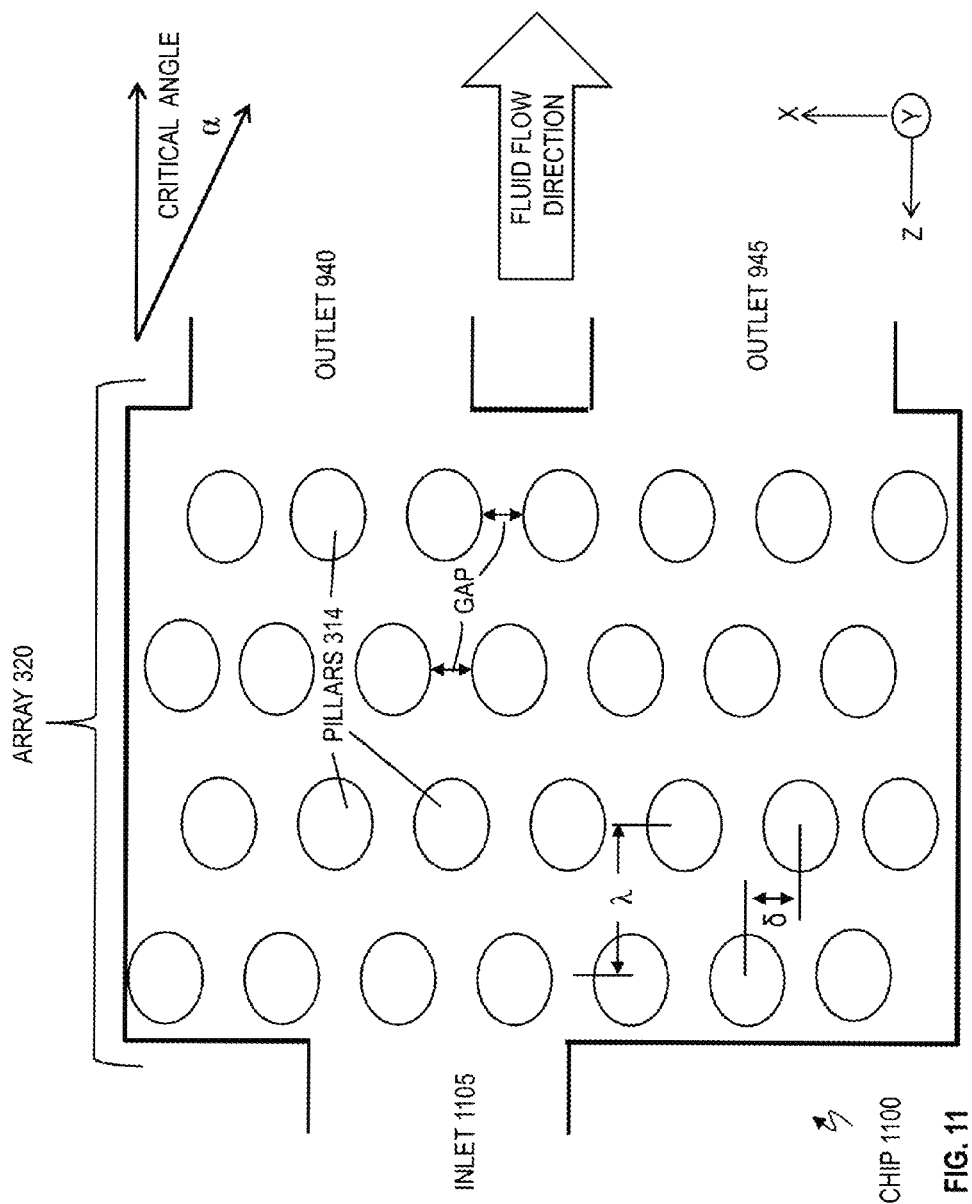
FIG. 11 is a top view illustrating a chip (fluidic device) having the pillar array according to an embodiment.

Use of the sub-headings is now discontinued. FIG. 11 illustrates a chip 1100 (fluidic device) having the pillar array 320 according to an embodiment. The chip 1100 has an inlet 1105 to receive fluid containing the different sized particles (i.e., biological entities) to be sorted. The inlet 1105 may be an opening or hole in the walls around the nanopillar array 320 or may span the width of the nanopillar array 320 through which fluid (e.g. water, electrolyte solutions, organic solvents, etc.) and particles (e.g., biological entities) can flow. Particles having a size greater than the critical dimension are bumped (i.e., bumped mode) through the pillar array 320 in the direction of the critical angle, and these particles larger than the critical dimension are collected at outlet 940. The critical dimension is the size (e.g., diameter) of a round shaped particle and/or persistence length of chain structure, such as DNA, that is too large to zigzag through the nanoarray 320. Particles having a size smaller than the critical dimension zigzag (i.e., zigzag mode) through the pillar array 320 in the direction of fluid flow, and these smaller particles are collected at the outlet 945. The particles having the size smaller than the critical dimension follow the direction of the fluid flow, and are sorted through the outlet 945. In one case, the pillars 314 may have the chemical modification as discussed herein, which can further reduce the gap size and/or sort particles having affinity to the chemical modification. The outlets 940 and 945 may be openings through which the sorted particles can flow and be collected in bins after sorting.

Figure 12:
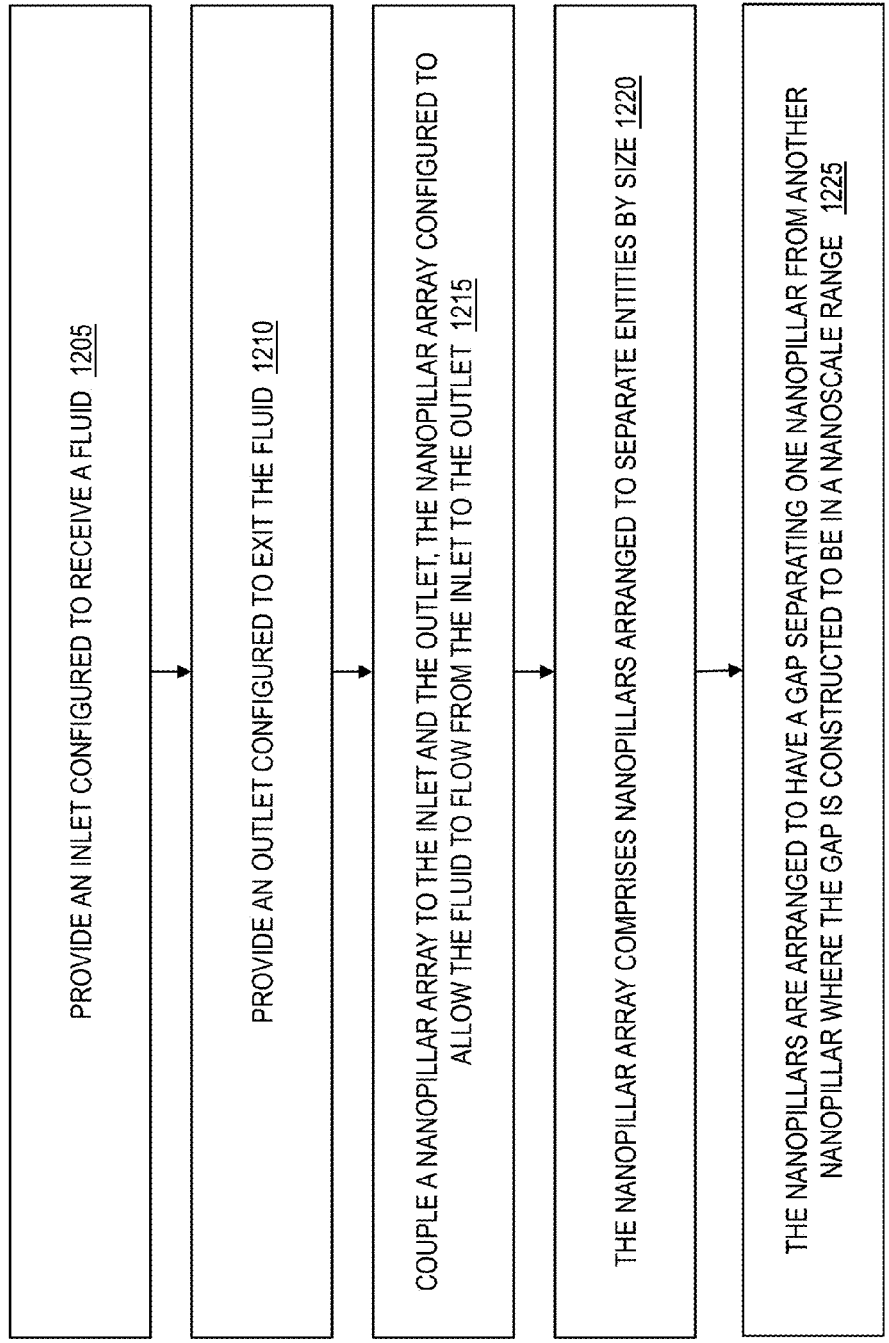
FIG. 12 is a method of providing a fluidic apparatus (e.g., chip) according to an embodiment.

FIG. 12 is a method 1200 of providing a fluidic apparatus 1100 (e.g., chip 1100) is provided according to an embodiment. Reference can be made to FIGS. 1-11 discussed above. At block 1205, the inlet 1105 is configured to receive a fluid. At block 1210, the outlet (e.g., outlets 940, 945) is configured to exit the fluid. The nanopillar array 320 is coupled to the inlet and the outlet, and the nanopillar array 320 is configured to allow the fluid to flow from the inlet to the outlet at block 1215.

At block 1220, the nanopillar array 320 comprises nanopillars 314 arranged to separate biological entities (particles) by size. At block 1225, the nanopillars 314 are arranged to have a gap G separating one nanopillar 314 from another nanopillar 314, and the gap is constructed to be in a nanoscale range (e.g., sub-100 nm).

The one nanopillar is to the side of the other nanopillar, such that the gap G is in between. The gap between the one nanopillar and the other nanopillar is uniform along a vertical axis of the one nanopillar and the other nanopillar (such as, e.g., gap G5 as shown in FIG. 10B).

The nanopillar array comprises an oxide layer 316 applied on the nanopillars, and the oxide layer 316 causes the gap to be uniform along a vertical axis of the one nanopillar and the another nanopillar (e.g., the gap G5 is uniform up and down the space between the two nanopillars 314 in FIG. 10B).

The oxide layer 316 causes a size of the gap (e.g., gap G5) to be as small as about 20 nanometers while the gap remains uniform along the vertical axis (e.g., y-axis in FIG. 10B). The oxide layer 316 causes unevenness in a diameter (e.g., the diameter of pillar 314 is not uniform in FIG. 10A) of the nanopillars to be uniform in FIG. 10B, resulting in the gap being uniform along the vertical axis of the one nanopillar and the other nanopillar. An increase in a thickness of the oxide layer 316 causes a decrease in a size of the gap.

In one case, the size of the gap ranges from 20-300 nm. In another case, the size of the gap may be formed to be less than 100 nm, may be less than 80 nm, may be less than 60 nm, may be less than 40, may be less than 30, may be less than 25, etc., according to the desired size of the particles to be separated. For example, 100 nm particles can be sorted/separated with 240 nm size gaps according to an embodiment.

A monolayer (e.g., the monolayer in FIGS. 7A, 7B, monolayer 815 in FIG. 8B, and/or monolayer 915 in FIG. 9A) is applied to the nanopillars 314 to reduce a size of the gap. The gap having a reduced size is configured to separate smaller entities relative to when the monolayer is not applied to the nanopillars.

Figure 13:
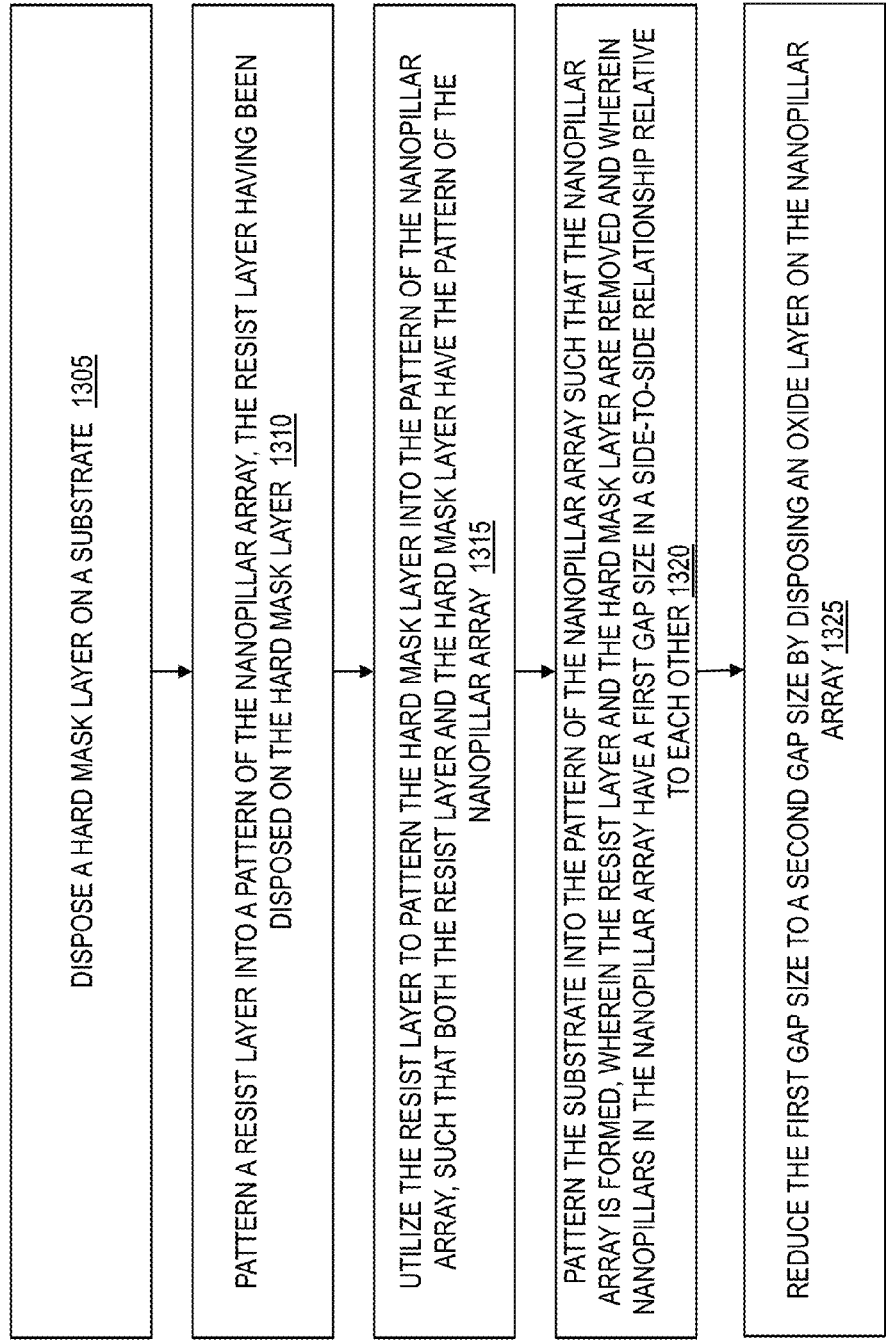
FIG. 13 is a method of forming a nanopillar array according to an embodiment.

FIG. 13 is a method 1300 of forming a nanopillar array 320 according to an embodiment. Reference can be made to FIGS. 1-12.

At block 1305, the hard mask layer 304 is disposed on the substrate 302. At block 1310, the resist layer 306 is patterned into a pattern (resist pattern 308) of the nanopillar array 320 in which the resist layer 306 was disposed on the hard mask layer 304.

At block 1315, the resist layer (resist pattern 308) is utilized to pattern the hard mask layer 304 into the pattern (hard mask pattern 312) of the nanopillar array 320, such that both the resist layer and the hard mask layer have the pattern of the nanopillar array 320.

At block 1320, the substrate 302 is patterned into the pattern of the nanopillar array 320 such that the nanopillar array 320 is now formed, wherein the resist layer (resist pattern 308) and the hard mask layer (hard mask pattern 312) are removed and wherein nanopillars 314 in the nanopillar array have a first gap size (e.g., gap size G1 and/or G2 in FIG. 10A) in a side-to-side relationship relative to each other. At block 1325, the first gap size is reduced to a second gap size (e.g., gap size G5) by disposing the oxide layer 316 on the nanopillar array 320.

The resist layer is patterned into the pattern (resist pattern 308) of the nanopillar array 320 by at least one of electron-beam lithography and/or nanoimprint lithography or another form of lithography.

Utilizing the resist layer to pattern the hard mask layer into the pattern of the nanopillar array comprises performing reactive ion etching to etch the hard mask into the pattern (hard mask pattern 312) of the nanopillar array 320.

Patterning the substrate 302 into the pattern of the nanopillar array such that the nanopillar array is formed comprises performing reactive ion etching to etch the substrate into the nanopillar array 320.

Reducing the first gap size (e.g., gap size G1 and G2) to the second gap size (gap size G5) by disposing the oxide layer 316 on the nanopillar array 320 comprises reducing the second gap size (e.g., to less than 300 nanometers, to less than 100 nanometers, etc.).

Reducing the first gap size to the second gap size by disposing the oxide layer on the nanopillar array causes each of the nanopillars to have a uniform shape and causes the second gap size to be uniform throughout the nanopillar array for the side-to-side relationship of the nanopillars (as shown in FIGS. 10A and 10B). Before reducing the first gap size to the second gap size by disposing the oxide layer, the nanopillars have an inward-bowed shape at a middle of the nanopillars at a nanoscale level. Reducing the first gap size to the second gap size by disposing the oxide layer both fills in the inward-bowed shape at the middle and straightens the nanopillars into a cylinder-like shape.

As discussed herein, embodiments provide silicon chips with nanopillars and nanogaps that can separate molecules and particles by size from the micron regime down to the nanometer regime. The size of two or more entities (particles) that can be separated depends on the size of the gaps (i.e., nanogaps) between the nanopillars. The state-of-the-art has no technologies for sorting entities by size in the 10-100 nm scale. However, embodiments described herein provide a mechanism for sorting entities within, above, and below this range (10-100 nm). For example, embodiments can sort a 30 nm particle from a 40 nm particle. Furthermore, embodiments provide continuous flow bio-separation, which means that particle sorting is continuous as fluid and the entities (to be separated) are introduced into one or more inlets of the nanopillar array 320, and the continuous flow bio-separation nanopillar array 320 continuously sorts the entities without requiring any type of reset.

For example, the technology of embodiments can be used to stream a solution mix through the chip 1100, obtaining a continuous separation of particles within a specified size range. A heterogeneous particle solution is introduced at the inlet of the chip 1100 and a solution flow carries the particles through a pillar network (i.e., pillar array 320). Particles of larger sizes bounce off the nanopillars 314 according to a preset angle (i.e., critical angle α) defined by the offset δ and the pitch λ of the nanopillars 314. In this way, the trajectory of the larger particles is directed (bump mode) toward a specific microchannel exit (e.g., outlet 940) where the separated sample can be extracted, while smaller particles will zigzag through the nanopillars 314 parallel to the direction of fluid flow where the smaller particles exit the chip 1100 through a different microchannel (e.g., outlet 945).

The improvements in embodiments allow for this type of continuous flow separation to operate at the nanometer scale, permitting efficient separation of bio-markers, biomolecules, sub-cellular components, exosomes, viruses, immuno-assays, drug screening, and protein aggregates on a Si chip (such as, e.g., chip 1100). Embodiments are a significant scale down from the micron scale in state-of-the-art. The improvement over the state-of-the-art was achieved through the nanofabrication of nanopillars capable of sorting particles at the nanoscale. Embodiments also demonstrate that, at this new scale, a different flow regime applies and improves the separation method. At this scale, dead flow areas between nanopilars are proportionally significant with respect to the nanopilar size. The presence of these dead flow areas contributes to a narrower fluidic gap between nanopillars than the physical gap (G) defined by the nanopillar wall to wall distance. This results in the ability to sort a particle size smaller to what the original theory predicts.

Figure 14:
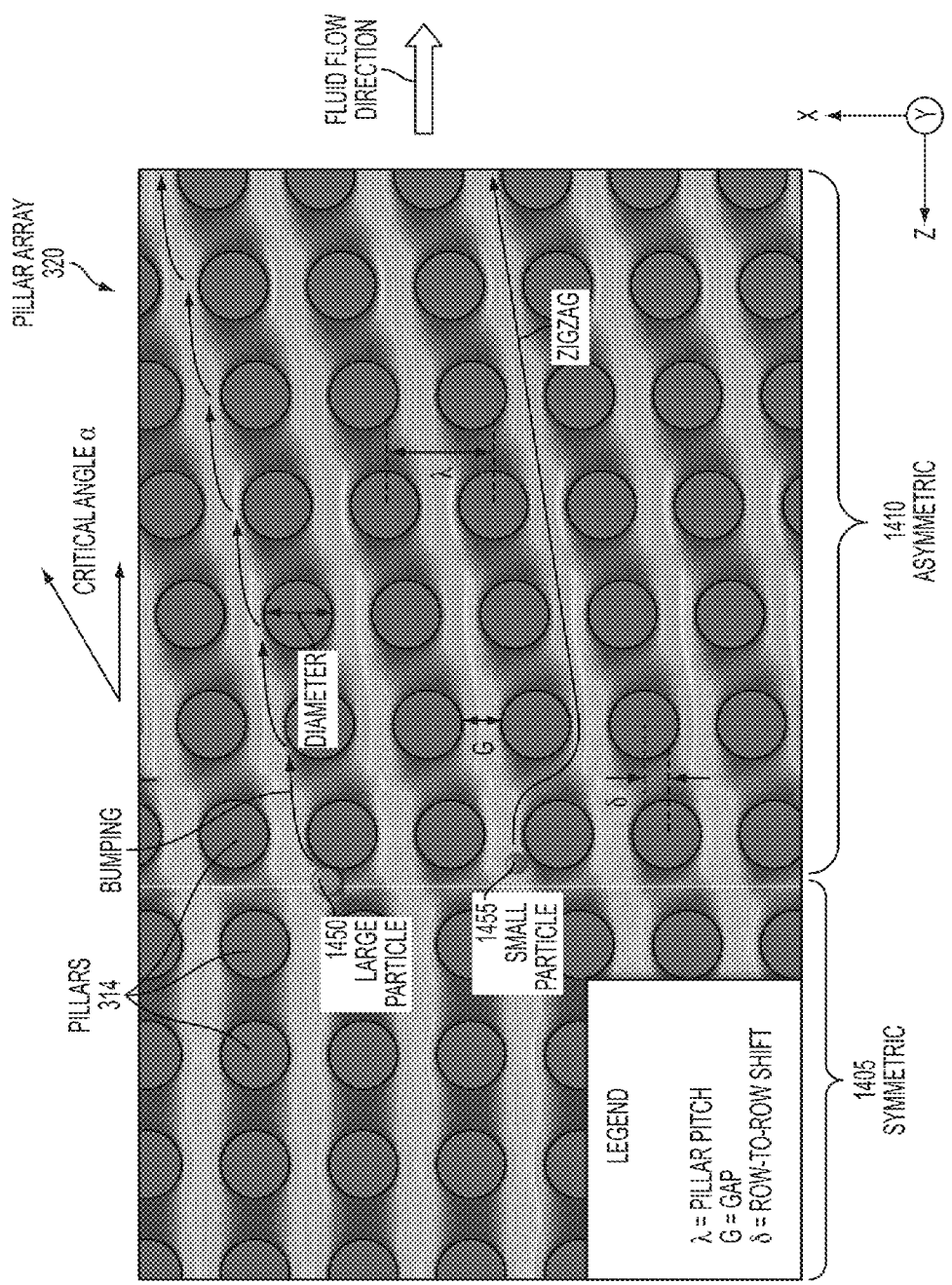
FIG. 14 is a top view of a schematic representing an arrangement of the pillars in the nanopillar array according to an embodiment.

FIG. 14 is a top view of a schematic representing an arrangement of the pillars 314 in the nanopillar array 320 according to an embodiment. In this example, the pillar array 320 may be considered as multiple pillar arrays. For example, the pillar array 320 includes a symmetric part/arrangement 1405 of pillars 314 and an asymmetric part/arrangement 1410 of pillars 314. The symmetric part 1405 has a critical angle that is (virtually) 0°, while the asymmetric part 1410 has a critical angle α (defined with respect to the z-axis in FIG. 14).

In FIG. 14, the flow stream (i.e., fluid flow direction) is horizontal on the average, and the pillar rows are tilted to an angle (i.e., forming the critical angle α) in the asymmetric part 1410 of the nanopillar array 320. At sufficiently slow flow rates of the fluid, the distance (gap G) between the pillars 314 together with the critical angle define the size (smaller than a critical dimension) of the particles that are able to follow the flow direction by zig-zagging through the pillars 314, and the size (equal to and/or greater than the critical dimension) of the particles that will be displaced (bumped) by the angle of the pillar rows. In one case, a slow flow rate may correspond to a flow slower than 500 μm/s.

The pillars 314 have a diameter, a pillar pitch λ, a gap (G), and a row-to-row shift (δ). The row-to-row shift (δ) is in the asymmetric part 1410 because there is no row-to-row shift in the symmetric part 1405. In the example of FIG. 14, two example particles of different sizes are traversing through the pillar array 320. The larger particle 1450 is displaced (indicated by a dash line) across the array 320 according to the pillar angle (i.e., critical angle α), while the smaller particle 1455 follows the deterministic flow (solid line) through the array 320 zig-zagging through the pillars 314.

Figure 15:
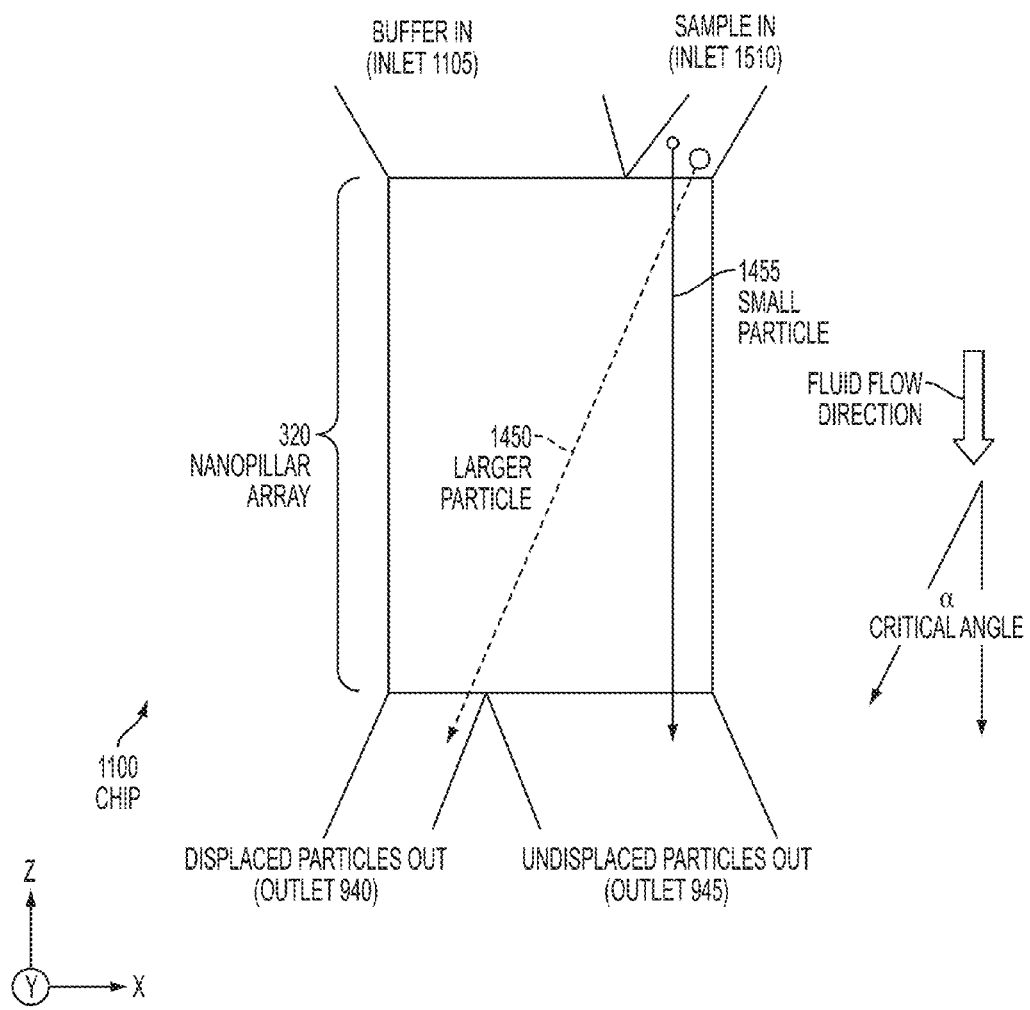
FIG. 15 is a schematic of the chip now with two inlets and with particles of different sizes traversing through the nanopillar array according to an embodiment.

FIG. 15 is a schematic of the chip 1100 now with two inlets and with two particles of different sizes traversing through the pillar array 320 according to an embodiment. The larger particle 1450 is displaced along the dashed line across the array 320 according to the pillar angle (critical angle), while the smaller particle 1455 follows the deterministic flow through the array by zig-zagging through the pillars 314. The large nanoparticle 1450 and the smaller nanoparticle 1455 exit the array through separate microfluidic channels. For example, the large nanoparticle 1450 (e.g., equal to and/or above the critical dimension) exits the array through outlet 940, while the small nanoparticle 1455 (e.g., below the critical dimension) exits the through outlet 945. In this example, the fluid, which may be a buffer solution, can be introduced through the buffer in inlet 1105. The buffer solution (also referred to as a pH buffer or hydrogen ion buffer) is an aqueous solution consisting of a mixture of a weak acid and its conjugate base, or vice versa. The sample, which includes the nanoparticles 1450 and 1455 to be sorted, is introduced through the same inlet 1510. Although only two particles are shown, the same sorting process applies to numerous particles having the different sizes introduced into the sample inlet 1510.

Figure 16A:
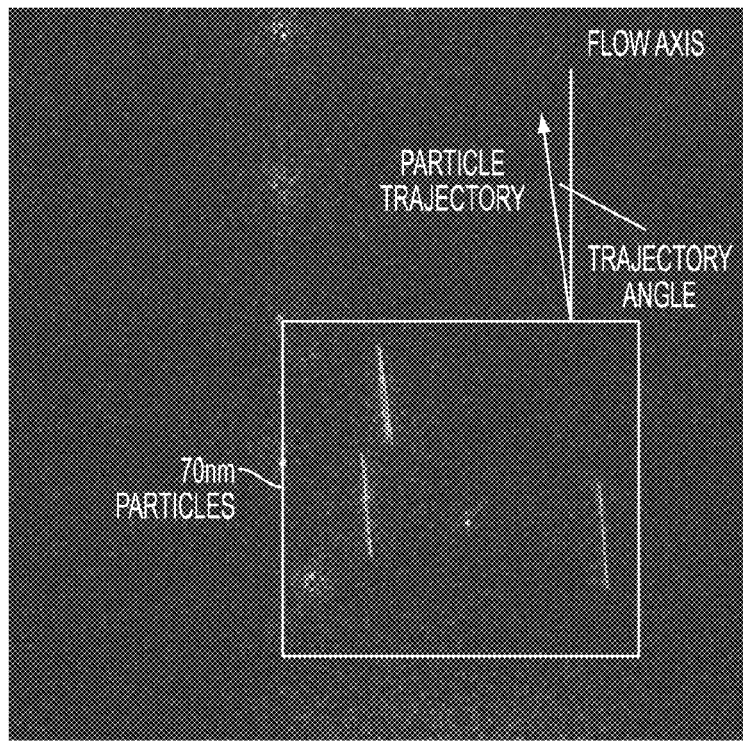
FIG. 16A is a scanning electron microscope image of particle trajectories for 70 nanometer diameter beads according to an embodiment.
Figure 16B:
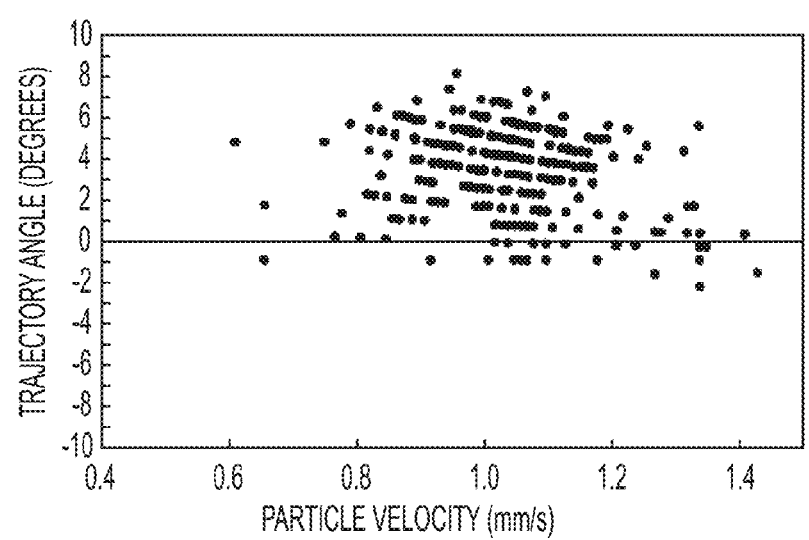
FIG. 16B is a plot of trajectory angle as a function of velocity for the 70 nanometer beads according to an embodiment.
Figure 16C:
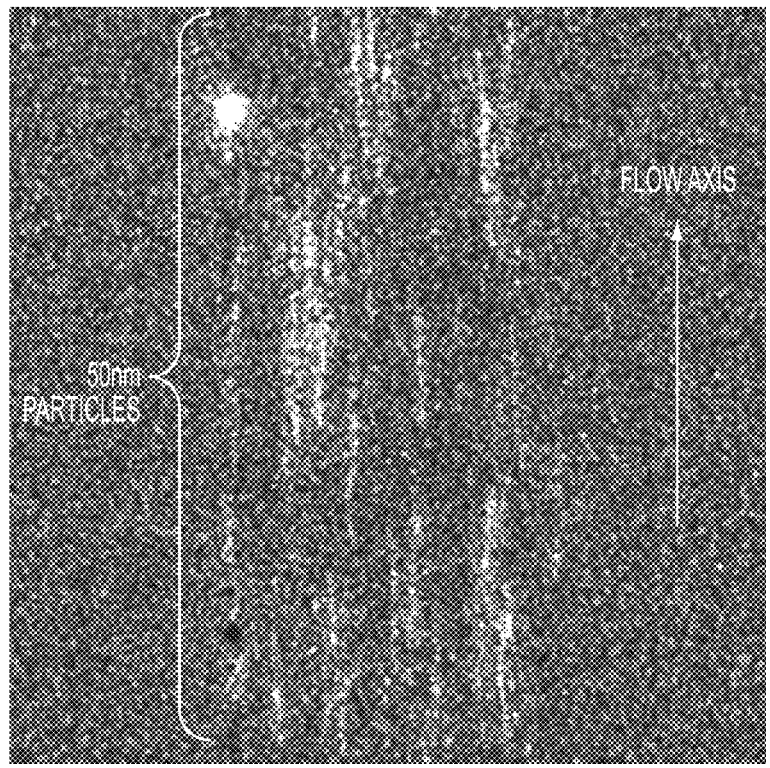
FIG. 16C is a scanning electron microscope image of particle trajectories for 50 nanometer diameter beads according to an embodiment.

FIGS. 16A, 16B, 16C, and 16B illustrate experimental results of passing two populations of nano-beads through the nanopillar array 320 according to an embodiment. FIGS. 16A and 16B correspond to a population of 70 nm diameter beads, while FIGS. 16C and 16D correspond to the population of 50 nm diameter beads. In FIGS. 16A and 16C the respective beads' trajectories are recorded with a video camera on a fluorescence microscope. In this example, the gap size (G) between the nanopillars 314 is 210 nm.

FIG. 16A is the image of particle trajectories for 70 nm beads being displaced in a 5.7° critical angle array (320). FIG. 16A shows that the bead trajectory of 70 nm diameter beads is angled with respect to the flow direction. The average trajectory angle observed for the 70 nm beads is a 5.7° angle. The marked trajectories of three 70 nm particles are shown. The angle between the flow direction (i.e., fluid flow direction) and particle trajectory describes the degree to which the particle is bumping in the array 320. For these 70 nm particles, a plot of trajectory angle as a function of velocity shows a positive value close to the critical angle in FIG. 16B. In other words, the average trajectory angle of the 70 nm beads plotted in FIG. 16B is approximately 5.7° which is expected for the 5.7° critical angle of the array 320 in the experiment.

Figure 16D:
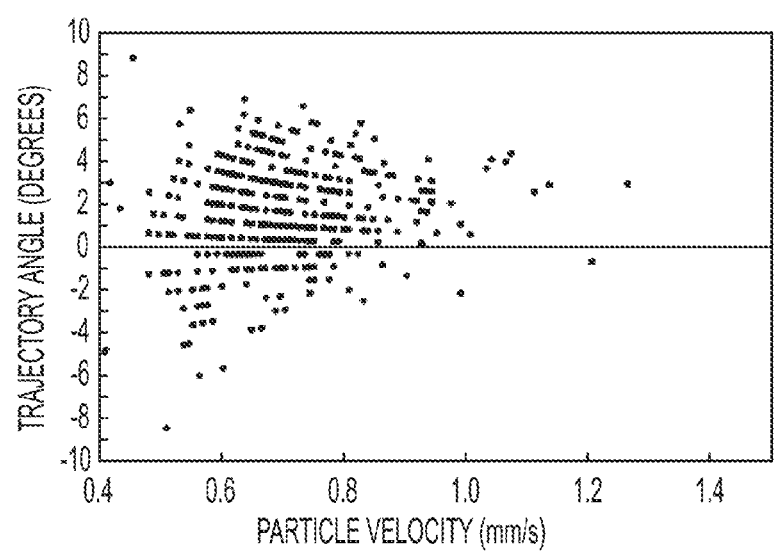
FIG. 16D is a plot of trajectory angle as a function of velocity for the 50 nanometer beads according to an embodiment.

FIG. 16C is the image of particle trajectories for 50 nm diameter beads sorted in the same array 320. Under the same conditions (including the same nanopillar array 320 with the 5.7° critical angle), the 50 nm beads are introduced in the array 320, and their trajectories are recorded in FIG. 16C. These 50 nm particles are not displaced (i.e., not in bump mode) in the array 320, which is observed in the trajectory angle and velocity plot in FIG. 16D. The plot in FIG. 16D shows a near-symmetric distribution of trajectory angles around 0° (i.e., in accord with the flow axis in the array 320). Also, FIG. 16C shows that the average trajectory angle followed by the 50 nm beads is close to 0°.

As seen in FIGS. 16A, 16B, 16C, and 16D, the nanopillar array 320 is configured to sort the 50 nm beads from the 70 nm beads, by outputting the 50 nm beads in a first direction along the flow axis, while outputting the 70 nm beads in a second direction along the critical angle of the pillar array 320.

FIG. 17 is a chart illustrating example data of the approximate gap sizes to separate a particle of one size from a particle of another size utilizing the nanopillar array 320 according to an embodiment. It is noted that the example data in chart in FIG. 17 is meant for illustration purposes and not limitation. The gap sizes (G) between the nanopillars are listed horizontally, and particle diameters are listed vertically. The result of each experiment is described as either No displacement, Partial displacement, or displacement 100%. Displacement 100% means that the trajectory angle of the particles over the array is the same as the set pillar critical angle, or within 15% of this angle. Partial displacement accounts for particles trajectories ranging from 15 to 85% of the nanopillar critical angle. No displacement represents any experiment were the trajectory angle of the particles is less than 15% of the nanopillar array critical angle.

In one implementation, embodiments rely on manufacturable (silicon) pillar arrays 320 with uniform gaps between the pillars and with dimensions in the sub-100 nm regime. These arrays 320 are for the sorting and separation of biological entities at these dimensions, such as DNA, RNA, exosomes, individual proteins, and protein complexes. Uniform gap sizes are utilized to obtain efficient sorting, e.g., to sort a 20 nm particle from a 10 nm particle according to embodiment. This is particularly challenging for gaps in the sub-100 nm regime where there could be inherent variations greater than the dimensions of the particles to be sorted. This is usually caused by non-uniform nanopatterning at this scale, and feature variations in sizes and shapes due to the reactive-ion etch (RIE) process. Demonstrated sorting pillar gaps found in the state-of-the-art have dimensions in the micron range and therefore cannot sort even close to this fine of a scale.

Therefore, consistent gaps in the nanometer regime are required to sort, for example, a protein aggregate. Sorting of individual proteins (size range of 1-10 nm) is traditionally performed using ion exchange chromatography or gel electrophoresis, which are load-and-run techniques rather than continuous flow and thus much slower. However, embodiments provide a continuous flow separation process and mechanism, which is configured to sort individual proteins (or other particles) in the range of 1-10 nm, without requiring ion exchange chromatography or gel electrophoresis.

FIG. 18 is a method 1800 for sorting entities according to an embodiment. Reference can be made to FIGS. 1-17.

At block 1805, the entities are introduced into the nanopillar array 320, and the entities include a first population and a second population. The nanopillar array 320 includes nanopillars 314 arranged to have a gap separating one from another, and the nanopillars are ordered to have an array angle relative to a fluid flow direction.

At block 1810, the entities are sorted through the nanopillar array 320 by transporting the first population of entities less than a predetermined critical size in a first direction (e.g., toward outlet 945) and by transporting the second population of entities at least the predetermined size in a second direction (e.g., toward outlet 940) different from the first direction.

At block 1815, the nanopillar array 320 is configured to employ the gap with a gap size less than 300 nanometers or less than 100 nanometers in order to sort the entities having a sub-100 nanometer size.

When the entities have a nanometer size equal to or greater than 7 nanometers, the nanopillar array is configured accordingly to sort the entities having the nanometer size equal to or greater than 7 nanometers. When the entities have a nanometer size equal to or greater than 7 nanometers, the gap size is configured accordingly to sort the entities having the nanometer size equal to or greater than 7 nanometers.

A lower limit of the gap size may be about 20 nanometers. A thickness of an oxide layer 316 applied to the nanopillar array 320 causes the gap size of the gap to be about 20 nanometers while the gap remains uniform. In other words, the gap is uniform along the vertical axis (e.g., y-axis) between any two nanopillars 314 (i.e., no gap variation), and each of the gaps throughout the nanopillar array 320 has the same gap size.

The gap size of the gap is tuned to sort the first population of the entities less than the predetermined critical size in the first direction while sorting the second population of the entities at least the predetermined size in the second direction. Tuning the gap size is based on a thickness of the oxide layer 316 applied to the nanopillar array 320. Further tuning the gap size can be based on a monolayer (e.g., without a metal applied in FIG. 7A, and/or with a metal applied in FIG. 7B) applied to the nanopillars by chemical modification. The chemical modification forms a monolayer (e.g., such as monolayer 815, 915) on the nanopillars 314 such that the first population has an affinity to the monolayer and the second population has no affinity to the monolayer. Having the affinity to the monolayer directs the first population (e.g., such as entities 910) of the entities to be transported in the first direction (e.g., to outlet 945). Not having the affinity to the monolayer allows the second population (e.g., such as entities 905) to be bumped in the second direction to outlet 940. In one case, both entities 905 and 910 may be about the same size, and the affinity of entities 910 causes the entities 910 to proceed toward the outlet 945. The entities comprise at least one of bio-markers, bio-molecules, sub-cellular components, exosomes, viruses, immuno-assays, and/or protein aggregates.

Exosomes are becoming more and more important science but are too small, e.g., 30-100 nm, to be sorted by state-of-the-art arrays. Exosomes are now believed to be present in all body fluids, and represent a new way of thinking about cell signaling. These small extracellular vesicles are thought to play a role in a large number of biological functions. For example, exosomes are a messaging system and regulation system, which may contain and transfer DNA, RNA, protein, etc. In the nanopillar array 320, the gap size can be narrowed by the oxide layer 316 to sort one size exosome from larger size exosome, and/or to sort the smaller exosome from a different (larger) particle. Additionally, exosomes have special affinity (i.e., attraction) to certain ligands. For example, a monolayer 815, 915 of the lipid membrane integrating ligands, such as [6-(pyren-2-yl) octyl]silane or 3-[(8-silyloctyl)oxy]cholesterol, can be applied to the pillars 314 to direct the exosomes in a first direction while directing the different particles in a second direction because the different particles do not have the special affinity. Therefore, even if the different particles have a same (or similar) size as the exosomes in one case, the exosomes can still be sorted because of their special affinity to the certain ligands. Although certain ligands having a special affinity to exosomes are discussed for explanation purposes, it is understood that the certain ligands having a special affinity to exosomes are not limited to these examples.

FIG. 19 is a method 1900 of sorting entities according to an embodiment. Reference can be made to FIGS. 1-18.

At block 1905, entities to be sorted are introduced into the nanopillar array 320 (e.g., via inlet 1105 and/or inlet 1510), and the entities include a first population and a second population. The nanopillar array 320 includes nanopillars 314 arranged to have a gap G separating one from another, and the nanopillars are ordered to have an array angle (e.g., critical angle) relative to a fluid flow direction.

At block 1910, the nanopillar array 320 is configured to receive the entities at the outlet (such as the outlet 940 and/or 945 where each outlet may be attached/coupled to a collection tray or collection bin) based on being sorted, such that the first population of the entities are output in a first direction and the second population of the entities are output in a second direction different from the first direction;

At block 1915, a gap size of the gap G is tuned to sort the first population in the first direction and the second population in the second direction, and the gap size is tuned according to at least one of a thickness of an oxide layer 316 disposed on the nanopillar array 320 and/or a chemical modification (such as in FIGS. 7-9) to the gap.

When the gap size is tuned by the oxide layer 316, the oxide layer 316 reduces the gap size to a first dimension. When the gap size is tuned by the chemical modification, the chemical modification further reduces the gap size to a second dimension, and the second dimension is smaller than the first dimension.

The first dimension corresponds to the oxide layer 316 reducing the gap size to about 20 nanometers while the gap remains uniform. The second dimension corresponds to the chemical modification (e.g., attached ligand) further reducing the gap size below 20 nanometers (e.g., after the oxide layer 316 has been deposited). For the second dimension, the chemical modification may reduce the gap size to 18, 16, 14, 12, and/or 10 nanometers. In one case, the chemical modification may reduce the gap size to below 10 nanometers as the second dimension. In another case, the chemical modification (using longer ligands) may reduce the gap size to 8, 6, 4, and/or 2 nanometers as the second dimension. If desired, the chemical modification can nearly close the gap by reducing the gap size to less than 2 nanometers as the second dimension.

When the gap size is tuned by the chemical modification, the chemical modification reduces the gap size to a first dimension. It is contemplated that the chemical modification may be applied to the nanopillars 314 even in a case when the oxide layer 316 is not applied.

The chemical modification forms a monolayer on the nanopillars such that the first population has an affinity to the monolayer and the second population has no affinity to the monolayer. Having the affinity to the monolayer directs the first population of the entities to be output in the first direction. The entities comprise at least one of bio-markers, bio-molecules, sub-cellular components, exosomes, viruses, immuno-assays, and/or protein aggregates.

According to an embodiment, FIG. 20 is a method 2000 of sorting entities. Reference can be made to FIGS. 1-19.

At block 2005, entities are introduced into the nanopillar array 320, and the entities including a first population and a second population. The nanopillar array 320 includes nanopillars 314 in an ordered arrangement. The nanopillars have a chemical modification. Various illustrations of chemical modifications have been discussed in FIGS. 7-9.

At block 2010, the output (e.g., outlets 940 and 945) receives the entities after sorting, such that the first population of the entities are output in a first direction (e.g., outlet 945 in FIG. 9A) based on the first population having an affinity to the chemical modification and the second population of the entities are output in a second direction (e.g., outlet 940 in FIG. 9A) different from the first direction. Also, there may be an operator who receives the sorted entities now separated into/through one or more outlets (outlets 940 and 945). The operator may utilize or attach separate collection apparatuses to separately receive and hold the collected entities.

The second population does not have the affinity to the chemical modification, such as entities 905 in FIG. 9A. By the second population not having the affinity to the chemical modification, the second population is output in the second direction (e.g., output outlet 940).

Deposition is any process that grows, coats, or otherwise transfers a material onto the wafer. Available technologies include, but are not limited to, thermal oxidation, physical vapor deposition (PVD), chemical vapor deposition (CVD), electrochemical deposition (ECD), molecular beam epitaxy (MBE) and more recently, atomic layer deposition (ALD) among others.

Removal is any process that removes material from the wafer: examples include etch processes (either wet or dry), and chemical-mechanical planarization (CMP), etc.

Patterning is the shaping or altering of deposited materials, and is generally referred to as lithography. For example, in conventional lithography, the wafer is coated with a chemical called a photoresist; then, a machine called a stepper focuses, aligns, and moves a mask, exposing select portions of the wafer below to short wavelength light; the exposed regions are washed away by a developer solution. After etching or other processing, the remaining photoresist is removed. Patterning also includes electron-beam lithography, nanoimprint lithography, and reactive ion etching.

The flowchart and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

What is claimed is:
1. A method for sorting entities, the method comprising:
   introducing the entities into a nanopillar array, the entities including a first population and a second population, wherein the nanopillar array includes nanopillars arranged to have a gap separating one from another, and wherein the nanopillars are ordered to have an array angle relative to a fluid flow direction;

sorting the entities through the nanopillar array by transporting the first population of the entities less than a predetermined size in a first direction and by transporting the second population of the entities at least the predetermined size in a second direction different from the first direction;

wherein the nanopillar array is configured to employ the gap with a gap size less than 300 nanometers in order to sort the entities having a sub-100 nanometer size;

wherein a cavity in the nanopillars is filled in by an oxide layer on the nanopillars such that the oxide layer is configured to cause the gap size of the gap to be uniform between the nanopillars.

2. The method of claim 1, wherein when the entities have a nanometer size equal to or greater than 7 nanometers, the nanopillar array is configured to sort the entities having the nanometer size equal to or greater than 7 nanometers.

3. The method of claim 1, wherein when the entities have a nanometer size equal to or greater than 7 nanometers, the gap size is configured to sort the entities having the nanometer size equal to or greater than 7 nanometers.

4. The method of claim 1, wherein a lower limit of the gap size is about 20 nanometers.

5. The method of claim 4, wherein a thickness of the oxide layer applied to the nanopillar array causes the gap size of the gap to be about 20 nanometers while the gap remains uniform.

6. The method of claim 1, wherein the gap size of the gap is tuned to sort the first population of the entities less than the predetermined size in the first direction while sorting the second population of the entities at least the predetermined size in the second direction;

wherein tuning the gap size is based on a thickness of the oxide layer applied to the nanopillar array.

7. The method of claim 6, wherein further tuning the gap size is based on a monolayer applied to the nanopillars by chemical modification.

8. The method of claim 1, wherein a chemical modification forms a monolayer on the nanopillars such that the first population has an affinity to the monolayer and the second population has no affinity to the monolayer;

wherein having the affinity to the monolayer directs the first population of the entities to be transported in the first direction.

9. The method of claim 1, wherein the entities comprise at least one of bio-markers, bio-molecules, sub-cellular components, exosomes, viruses, immuno-assays, and protein aggregates.

* * * * *